(12) United States Patent
Maher et al.

(10) Patent No.: US 10,899,818 B2
(45) Date of Patent: *Jan. 26, 2021

(54) THERAPEUTIC AGENTS

(71) Applicant: KING'S COLLEGE LONDON, London (GB)

(72) Inventors: John Maher, London (GB); Daniela Yordanova Achkova, London (GB); Lynsey May Whilding, London (GB); Benjamin Owen Draper, London (GB)

(73) Assignee: King's College London, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/877,008

(22) Filed: May 18, 2020

(65) Prior Publication Data
US 2020/0331981 A1  Oct. 22, 2020

Related U.S. Application Data

(63) Continuation of application No. 15/749,016, filed as application No. PCT/GB2016/052324 on Jul. 28, 2016, now Pat. No. 10,703,794.

(30) Foreign Application Priority Data

Jul. 31, 2015 (GB) .................. 1513540.3

(51) Int. Cl.
| | | |
|---|---|---|
| *A01N 63/00* | (2020.01) | |
| *A61K 48/00* | (2006.01) | |
| *C07K 14/725* | (2006.01) | |
| *C07K 14/53* | (2006.01) | |
| *C07K 14/54* | (2006.01) | |
| *C07K 14/705* | (2006.01) | |
| *C12N 5/0783* | (2010.01) | |

(52) U.S. Cl.
CPC .......... *C07K 14/7051* (2013.01); *C07K 14/53* (2013.01); *C07K 14/54* (2013.01); *C07K 14/705* (2013.01); *C07K 14/70517* (2013.01); *C07K 14/70521* (2013.01); *C07K 14/70578* (2013.01); *C12N 5/0636* (2013.01); *C07K 2319/00* (2013.01); *C07K 2319/02* (2013.01); *C07K 2319/03* (2013.01); *C07K 2319/33* (2013.01)

(58) Field of Classification Search
CPC .. C07K 14/7051; C07K 14/705; C07K 14/53; C12N 5/0636
USPC ..................................................... 424/93.21
See application file for complete search history.

(56) References Cited

U.S. PATENT DOCUMENTS

| | | | |
|---|---|---|---|
| 7,446,190 B2 | 11/2008 | Sadelain et al. | |
| 8,383,593 B2 | 2/2013 | Howard et al. | |
| 8,389,282 B2 | 3/2013 | Sadelain et al. | |
| 8,927,501 B2 | 1/2015 | Howard | |
| 9,783,591 B2 | 10/2017 | June | |
| 9,833,476 B2 | 12/2017 | Zhang et al. | |
| 2014/0099309 A1 | 4/2014 | Powell, Jr. et al. | |
| 2014/0286987 A1 | 9/2014 | Spencer et al. | |
| 2017/0360913 A1 | 12/2017 | Zhao et al. | |

FOREIGN PATENT DOCUMENTS

| | | |
|---|---|---|
| WO | 2008/121420 A1 | 10/2008 |
| WO | 2010/085660 A2 | 7/2010 |
| WO | 2011/041093 A1 | 4/2011 |
| WO | 2012/129514 A1 | 9/2012 |
| WO | 2013/019615 A2 | 2/2013 |
| WO | 2013/126733 A1 | 8/2013 |
| WO | 2013/185552 A1 | 12/2013 |
| WO | 2014/039523 A1 | 3/2014 |
| WO | 2014/055442 A2 | 4/2014 |
| WO | 2014/055657 A1 | 4/2014 |
| WO | 2014/055668 A1 | 4/2014 |
| WO | 2014/124143 A1 | 8/2014 |
| WO | 2014/127261 A1 | 8/2014 |
| WO | 2014/138348 A1 | 9/2014 |
| WO | 2014/164544 A1 | 10/2014 |
| WO | 2014/172584 A1 | 10/2014 |
| WO | 2015/066551 A2 | 5/2015 |
| WO | 2015/075468 A1 | 5/2015 |
| WO | 2015/090229 A1 | 6/2015 |
| WO | 2015/164627 A1 | 10/2015 |
| WO | 2016/011210 A2 | 1/2016 |
| WO | 2016/014565 A2 | 1/2016 |

(Continued)

OTHER PUBLICATIONS

Dotti (Jan. 2014, Immunol. Rev., 257(1), pp. 1-35.*

(Continued)

*Primary Examiner* — Valarie E Bertoglio

(57) ABSTRACT

An immunoresponsive cell, such as a T-cell expressing
 (i) a second generation chimeric antigen receptor comprising:
  (a) a signalling region;
  (b) a co-stimulatory signalling region;
  (c) a transmembrane domain; and
  (d) a binding element that specifically interacts with a first epitope on a target antigen; and
 (ii) a chimeric costimulatory receptor comprising
  (e) a co-stimulatory signalling region which is different to that of (b);
  (f) a transmembrane domain; and
  g) a binding element that specifically interacts with a second epitope on a target antigen.

This arrangement is referred to as parallel chimeric activating receptors (pCAR). Cells of this type are useful in therapy, and kits and methods for using them as well as methods for preparing them are described and claimed.

29 Claims, 27 Drawing Sheets

Specification includes a Sequence Listing.

(56) References Cited

FOREIGN PATENT DOCUMENTS

| WO | 2016/122738 A1 | 8/2016 |
|---|---|---|
| WO | 2016/196388 A1 | 12/2016 |
| WO | 2017/021701 A1 | 2/2017 |

OTHER PUBLICATIONS

Alvarez-Vallina et al., "Antigen-specific targeting of CD28-mediated T cell co-stimulation using chimeric single-chain antibody variable fragment-CD28 receptors," Eur. J. Immunol., 1996, pp. 2304-2309, vol. 26.

Blanco et al., "Autocrine costimulation: Tumor-specific CD28-mediated costimulation of T cells by in situ production of a bifunctional B7-anti-CEA diabody fusion protein," Cancer Gene Therapy, 2002, pp. 275-281, vol. 9.

Carpenito et al., "Control of large, established tumor xenografts with genetically retargeted human T cells containing CD28 and CD137 domains," PNAS, 2009, pp. 3360-3365, vol. 106, No. 9.

Cartellieri et al., "Chimeric Antigen Receptor-Engineered T Cells for Immunotherapy of Cancer," Journal of Biomedicine and Biotechnology, 2010, pp. 1-13, vol. 2010.

Ding et al., "Activation of CD4+ T cells by delivery of the B7 costimulatory signal on bystander antigen-presenting cells (trans-costimulation)," Eur. J. Immunol., 1994, pp. 859-886. vol. 24.

Finney et al., "Chimeric Receptors Providing Both Primary and Costimulatory Signaling in T Cells from a Single Gene Product," The Journal of Immunology, 1998, pp. 2791-2797, vol. 161.

Geiger et al., "Integrated src kinase and costimulatory activity enhances signal transduction through single-chain chimeric receptors in T lymphocytes," Blood, 2001, pp. 2364-2371, vol. 98, No. 8.

Guedan et al., "ICOS-based chimeric antigen receptors program bipolar TH17/TH1 cells," Blood, 2014, pp. 1070-1080, vol. 124, No. 7.

Haynes et al., "Single-chain antigen recognition receptors that costimulate potent rejection of established experimental tumors." Blood, 2002, pp. 3165-3163, vol. 100.

Hombach et al., "Tumor-Specific T Cell Activation by Recombinant Immunoreceptors: CD3 Signaling and CD28 Costimulation Are Simultaneously Required for Efficient IL-2 Secretion and Can Be Integrated Into One Combined CD28/CD3 Signaling Receptor Molecule," The Journal of Immunology, 2001, pp. 6123-6131, vol. 167.

Hombach et al., "Costimulation tunes tumor-specific activation of redirected T cells in adoptive immunotherapy," Cancer Immunol Immunother, 2007, pp. 731-737, vol. 56.

Hombach et al., "Young T cells age during a redirected anti-tumor attack: chimeric antigen receptor-provided dual costimulation is half the battle," Frontiers in Immunology, 2013, pp. 1-4, vol. 4.

International Search Report and Written Opinion from International Application No. PCT/GB2016/052324, dated Oct. 7, 2016; 12 pgs.

Kieback et al., "A safeguard eliminates T cell receptor gene-modified autoreactive T cells after adoptive transfer," PNAS, 2008, pp. 623-628, vol. 105, No. 2.

Kloss et al., "Combinatorial antigen recognition with balanced signaling promotes selective tumor eradication by engineered T cells," Nature Biotechnology, 2013, pp. 71-75, vol. 31, No. 1.

Lantis et al., "Chimeric antigen receptor T cells with dissociated signaling domains exhibit focused anti-tumor activity with reduced potential for toxicity in vivo," Cancer Immunology Research, 2013, pp. 43-53, vol. 1, No. 1.

Liu et al., "A Chimeric Switch-Receptor Targeting PD1 Augments the Efficacy of Second-Generation CAR T Cells in Advanced Solid Tumors," Cancer Research, 2016, pp. 1578-1590, vol. 76, No. 6.

Lo et al., "Harnessing the tumour-derived cytokine, CSF-1, to co-stimulate T-cell growth and activation," Molecular Immunology, 2008, pp. 1276-1287, vol. 45.

Long et al., "4-1BB Costimulation Ameliorates T Cell Exhaustion Induced by Tonic Signaling of Chimeric Antigen Receptors," Nat Med., 2015, pp. 581-590, vol. 21, No. 6.

Love et al., "ITAM-mediated Signaling by the T-Cell Antigen Receptor," Cold Spring Harbor Perspectives in Biology, 2010, a002485, pp. 1-9, vol. 2, No. 6.

Marti et al., "Negative-Feedback Regulation of CD28 Costimulation by a Novel Mitogen-Activated Protein Kinase Phosphatase, MKP6," The Journal of Immunology, 2001, pp. 197-206, vol. 166.

Orlandi et al., "Cloning immunoglobulin variable domains for expression by the polymerase chain reaction," PNAS, 1989, pp. 3833-3837, vol. 86.

Pace et al., "A Helix Propensity Scale Based on Experimental Studies of Peptides and Proteins," Biophysical Journal, 1998, pp. 422-427, vol. 75.

Pameijer et al., "Conversion of a tumor-binding peptide identified by phage display to a functional chimeric T cell antigen receptor," Cancer Gene Therapy, 2007, pp. 91-97, vol. 14.

Rudd et al., "Independent CD28 signalingvia VAV and SLP-76: a model for in trans costimulation," Immunological Reviews, 2003, pp. 32-41, vol. 192.

Sadelain et al., "The basic principles of chimeric antigen receptor (CAR) design," Cancer Discov., 2013, pp. 388-398, vol. 3, No. 4.

Sanchez-Lockhart et al., "Engagement of CD28 Outside of the Immunological Synapse Results in Up-Regulation of IL-2 mRNA Stability but Not IL-2 Transcription," The Journal of Immunology, 2006, pp. 4778-4784, vol. 176.

Savoldo et al., "CD28 costimulation improves expansion and persistence of chimeric antigen receptor-modified T cells in lymphoma patients," The Journal of Clinical Investigation, 2011, pp. 1822-1826, vol. 121, No. 5.

Sharma et al., "Tumor cells engineered to codisplay on their surface 4-1BBL and LIGHT costimulatory proteins as a novel novel vaccine approach for cancer immunotherapy," Cancer Gene Ther., 2010, pp. 730-741, vol. 17, No. 10.

Stephan et al., "T cell-encoded CD80 and 4-1BBL induce auto- and transcostimulation, resulting in potent tumor rejection," Nature Medicine, 2007, pp. 1-10.

Wang et al., "Optimizing Adoptive Polyclonal T Cell Immunotherapy of Lymphomas, Using a Chimeric T Cell Receptor Possessing CD28 and CD137 Costimulatory Domains," Human Gene Therapy, 2007, pp. 712-725, vol. 18.

Wilkie et al., "Dual Targeting of ErbB2 and MUC1 in Breast Cancer Using Chimeric Antigen Receptors Engineered to Provide Complementary Signaling," Journal of Clinical Immunology, 2012. pp. 1059-1070, vol. 32.

Zhao et al., "Structural Design of Engineered Costimulation Determines Tumor Rejection Kinetics and Persistence of CAR T Cells," Cancer Cell, 2015, pp. 415-428, vol. 28.

Zhong et al., "Chimeric Antigen Receptors Combining 4-1BB and CD28 Signaling Domains Augment PI3kinase/ AKT/ Bcl-XL Activation and CD8+ T Cell-mediated Tumor Eradication," Molecular Therapy, 2010, pp. 413-420, vol. 18, No. 2.

Notice of Reasons for Refusal, Japanese Patent Application No. 2018-503642, dated May 19, 2020; 4 pgs.

Capsomidis et al., "Chimeric Antigen Receptor-Engineered Human Gamma Delta T Cells: Enhanced Cytotoxicity with Retention of Cross Presentation," Molecular Therapy, 2018, pp. 354-365, vol. 26, No. 2.

Davies et al., "Flexible Targeting of ErbB Dimers That Drive Tumorigenesis by Using Genetically Engineered T Cells," Molecular Medicine, 2012, pp. 565-576, vol. 18.

Liu et al., "Use of CAR-Transduced Natural Killer Cells in CD19-Positive Lymphoid Tumors," The New England Journal of Medicine, 2020, pp. 545-553, vol. 382, No. 6.

Oberschmidt et al., "Redirected Primary Human Chimeric Antigen Receptor Natural Killer Cells As an "Off-the-Shelf Immunotherapy" for Improvement in Cancer Treatment," Frontiers in Immunology, 2017, pp. 1-9, vol. 8, No. 654.

Wang et al., "Glioblastoma-targeted CD4+ CAR T cells mediate superior antitumor activity," JCI Insight, 2018, e99048, pp. 1-18, vol. 3, No. 10.

Achkova et al., "Role of the colony-stimulating factor (CSF)/CSF-1 receptor axis in cancer," Biochemical Society Transactions, 2016, pp. 333-341, vol. 44, No. 2.

(56) References Cited

OTHER PUBLICATIONS

Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Research, 2011, pp. 5697-5706, vol. 71, No. 17.
Curran et al., "Enhancing Antitumor Efficacy of Chimeric Antigen Receptor T Cells Through Constitutive CD40L Expression," Molecular Therapy, 2015, pp. 769-778, vol. 23, No. 4.
Eshhar et al., "Specific activation and targeting of cytotoxic lymphocytes through chimeric single chains consisting of antibody-binding domains and the y or δ subunits of the immunoglobulin and T-cell receptors," PNAS, 1993, pp. 720-724, vol. 90, No. 2.
Fedorov et al., "PD-1-and CTLA-4-Based Inhibitory Chimeric Antigen Receptors (iCARs) Divert Off-Target Immunotherapy Responses," Sci Transl Med., 2013, 215ra172, pp. 1-25, vol. 5, No. 215.
Gibberd, Review of "GLOBOCAN 1: Cancer Incidence and Mortality Worldwide," Ferlay et al., IARC Press, Lyon, Statist. Med., 2000, pp. 2714-2715, vol. 19.
Finney et al., "Activation of Resting Human Primary T Cells with Chimeric Receptors: Costimulation from CD28, Inducible Costimulator, CD134, and CD137 in Series with Signals from the TCR Chain," The Journal of Immunology, 2004, pp. 104-113, vol. 172, No. 1.
Flick et al., "Recognition of activated CSF-1 receptor in breast carcinomas by a tyrosine 723 phosphospecific antibody," Oncogene, 1997, pp. 2553-2561, vol. 14, No. 21.
Foster et al., "Inducible MyD88/CD40 Allows AP1903-Dependent Costimulation to Control Proliferation and Survival of Chimeric Antigen Receptor-Modified T Cells," Blood, 2014, 1 page, vol. 124, No. 1121.
Grada et al., "TanCAR: A Novel Bispecific Chimeric Antigen Receptor for Cancer Immunotherapy," Molecular Therapy—Nucleic Acids, 2013: e105, pp. 1-11, vol. 2.
Imai et al., "Chimeric receptors with 4-1BB signaling capacity provoke potent cytotoxicity against acute lymphoblastic leukemia," Leukemia, 2004, pp. 676-684. vol. 18, No. 4.
Kluger et al., "Macrophage Colony-Stimulating Factor-1 Receptor Expression Is Associated with Poor Outcome in Breast Cancer by Large Cohort Tissue Microarray Analysis," Clinical Cancer Research, 2004, pp. 173-177, vol. 10, No. 1.
Krause et al., "Antigen-dependent CD28 Signaling Selectively Enhances Survival and Proliferation in Genetically Modified Activated Human Primary T Lymphocytes," J. Exp. Med., 1998, pp. 619-626, vol. 188, No. 4.
Maher et al., "Human T-lymphocyte cytotoxicity and proliferation directed by a single chimeric TCR CD28 receptor," Nature Biotechnology, 2002, pp. 70-75, vol. 20, No. 1.
Patsialou et al., "Autocrine CSF1R signaling mediates switching between invasion and proliferation downstream of TGFB in claudin-low breast tumor cells," Oncogene, 2015, pp. 2721-2731, vol. 34, No. 21.
Pegram et al., "Tumor-targeted T cells modified to secrete IL-12 eradicate systemic tumors without need for prior conditioning," Blood, 2012, pp. 4133-4141, vol. 119, No. 18.
Pule et al., "A Chimeric T Cell Antigen Receptor That Augments Cytokine Release and Supports Clonal Expansion of Primary Human T Cells," Molecular Therapy: 2005, pp. 933-941, vol. 12, No. 5.
Roybal et al., "Precision Tumor Recognition by T Cells With Combinatorial Antigen-Sensing Circuits," Cell, 2016, pp. 1-10, vol. 164.
Stortelers et al., "Epidermal Growth Factor Contains Both Positive and Negative Determinants for Interaction with ErbB-2/ErbB-3 Heterodimers," Biochemistry, 2002, pp. 4292-4301, vol. 41, No. 13.
Third Party Observation filed in EP Application No. 20 160750211.1, on May 31, 2019; 13 pgs.
Turtle et al., "Immunotherapy of non-Hodgkin's lymphoma with a defined ratio of CD8+ and CD4+ CD19-specific chimeric antigen receptor-modified T cells," Science Translational Medicine, 2016, pp. 1-12, vol. 8, No. 355.
Van der Stegen et al., "Preclinical In Vivo Modeling of Cytokine Release Syndrome Induced by ErbB-Retargeted Human T Cells: Identifying a Window of Therapeutic Opportunity?," The Journal of Immunology, 2013, pp. 4589-4598, vol. 191, No. 9.
Whilding et al., "Targeting of Aberrant avB6 integrin Expression in Solid Tumors Using Chimeric Antigen Receptor-Engineered T Cells," Molecular Therapy, 2017, pp. 259-273, vol. 25, No. 1.
Whilding et al., "The integrin avB6: a novel target for CAR T-cell immunotherapy?," Biochemical Society Transactions, 2016, pp. 349-355, vol. 44, No. 2.
Wilkie et al., "Selective Expansion of Chimeric Antigen Receptor-targeted T-cells with Potent Effector Function using Interleukin-4," The Journal of Biological Chemistry, 2010, pp. 25538-25544, vol. 285, No. 33.
Wilkie et al., "Retargeting of Human T Cells to Tumor-Associated MUC1: The Evolution of a Chimeric Antigen Receptor," The Journal of Immunology, 2008, pp. 4901-4909, vol. 180, No. 7.
Chmielewski et al., "T Cell Activation by Antibody-Like Immunoreceptors: Increase in Affinity of the Single-Chain Fragment Domain above Threshold Does Not Increase T Cell Activation against Antigen-Positive Target Cells but Decreases Selectivity", The Journal of Immunology, 2004, pp. 7647-7653, vol. 173.
Ghorashian et al., "Enhanced CAR T cell expansion and prolonged persistence in pediatric patients with ALL treated with a low-affinity CD19 CAR", Nature Medicine, 2019, pp. 1408-1414, vol. 25.
Lin et al., "Discovery of a Cytokine and Its Receptor by Functional Screening of the Extracellular Proteome", Science, 2008, pp. 807-811, vol. 320.
Schmid et al., "Evidence for a TCR Affinity Threshold Delimiting Maximal CD8 T Cell Function", The Journal of Immunology, 2010, pp. 4936-4946, vol. 184.
Thomas et al., "Human T cells expressing affinity-matured TCR display accelerated responses but fail to recognize low density of MHC-peptide antigen", Blood, 2011, pp. 319-329, vol. 118.
English translation of Office Action and Search Report from corresponding RU application No. 2018105137/10, dated Jan. 14, 2020; 7 pgs.
L. Jeger «Klinicheskaja immunologija I allergologija», 2nd ed., M.: Meditsina, 1990, vol. 1, pp. 219-222, (English translation—1 page).
Shi et al., "Chimeric antigen receptor for adoptive immunotherapy of cancer: latest research and future prospects", Molecular Cancer, 2014, pp. 1-8, vol. 13.

\* cited by examiner

THERAPEUTIC AGENTS

CROSS-REFERENCE TO RELATED APPLICATIONS

This application is a continuation application of U.S. application Ser. No. 15/749,016, filed Jan. 30, 2018, which is a 371 of International Patent Application No. PCT/GB2016/052324, filed Jul. 28, 2016, which claims the benefit of GB Application No. 1513540.3, filed Jul. 31, 2015, the disclosure of each is hereby incorporated by reference in its entirety.

INCORPORATION BY REFERENCE OF SEQUENCE LISTING

This application contains a Sequence Listing that has been submitted in ASCII format via EFS-Web and is hereby incorporated by reference in its entirety. The ASCII copy, created on Jun. 11, 2016, is named Sequence_Listing.txt, and is 8000 bytes in size.

FIELD OF THE INVENTION

The present invention relates to nucleic acids encoding novel chimeric antigen receptors (CARs), as well as to the CARs themselves, cells incorporating the nucleic acids and their use in therapy, in particular to methods in which they are used to facilitate a T-cell response to a selected target.

BACKGROUND OF THE INVENTION

Chimeric antigen receptors (CARs), which may also be referred to as artificial T cell receptors, chimeric T cell receptors (TCR) or chimeric immunoreceptors are engineered receptors, are well known in the art. They are used primarily to transform immune effector cells, in particular T-cells, so as to provide those cells with a particular specificity. They are particularly under investigation in the field of cancer immunotherapy where they may be used in techniques such as adoptive cell transfer. In these therapies, T-cells are removed from a patient and modified so that they express receptors specific to the antigens found in a particular form of cancer. The T cells, which can then recognize and kill the cancer cells, are reintroduced into the patient.

First generation CARs provide a TCR-like signal, most commonly using CD3 zeta (z) and thereby elicit tumouricidal functions. However, the engagement of CD3z-chain fusion receptors may not suffice to elicit substantial IL-2 secretion and/or proliferation in the absence of a concomitant co-stimulatory signal. In physiological T-cell responses, optimal lymphocyte activation requires the engagement of one or more co-stimulatory receptors (signal 2) such as CD28 or 4-1BB. Consequently, T cells have also been engineered so that they receive a co-stimulatory signal in a tumour antigen-dependent manner.

An important development in this regard has been the successful design of 'second generation CARs' that transduce a functional antigen-dependent co-stimulatory signal in human primary T cells, permitting T-cell proliferation in addition to tumouricidal activity. Second generation CARs most commonly provide co-stimulation using modules derived from CD28 or 4-1BB. The combined delivery of co-stimulation plus a CD3 zeta signal renders second generation CARs clearly superior in terms of function, when compared to their first generation counterparts (CD3z signal alone). An example of a second generation CAR is found in U.S. Pat. No. 7,446,190.

More recently, so-called 'third generation CARs' have been prepared. These combine multiple signalling domains, such as CD28+4-1BB+CD3z or CD28+OX40+CD3z, to further augment potency. In the 3rd generation CARs, the signalling domains are aligned in series in the CAR endodomain and placed upstream of CD3z.

In general however, the results achieved with these third generation CARs have disappointingly represented only a marginal improvement over 2nd generation configurations.

The use of cells transformed with multiple constructs has also been suggested. For example, Kloss et al. Nature Biotechnology 2012, doi:10.1038/nbt.2459 describes the transduction of T-cells with a CAR comprising a signal activation region (CD3 zeta chain) that targets a first antigen and a chimeric co-stimulatory receptor (CCR) comprising both CD28 and 4-1BB costimulatory regions which targets a second antigen. The two constructs bind to their respective antigens with different binding affinities and this leads to a 'tumour sensing' effect that may enhance the specificity of the therapy with a view to reducing side effects.

It is desirable to develop systems whereby T-cells can be maintained in a state that they can grow, produce cytokines and deliver a kill signal through several repeated rounds of stimulation by antigen-expressing tumour target cells. Provision of sub-optimal co-stimulation causes T-cells to lose these effector functions rapidly upon re-stimulation, entering a state known as "anergy". When CAR T-cells are sequentially re-stimulated in vitro, they progressively lose effector properties (e.g. IL-2 production, ability to proliferate) and differentiate to become more effector-like—in other words, less likely to manifest the effects of co-stimulation. This is undesirable for a cancer immunotherapy since more differentiated cells tend to have less longevity and reduced ability to undergo further growth/activation when they are stimulated repeatedly in the tumour microenvironment.

SUMMARY OF THE INVENTION

The applicants have found that effective T-cell responses may be generated using a combination of constructs in which multiple co-stimulatory regions are arranged in distinct constructs.

According to a first aspect of the present invention, there is provided an immuno-responsive cell expressing
  (i) a second generation chimeric antigen receptor comprising:
    (a) a signalling region;
    (b) a co-stimulatory signalling region;
    (c) a transmembrane domain; and
    (d) a binding element that specifically interacts with a first epitope on a target antigen; and
  (ii) a chimeric costimulatory receptor comprising
    (e) a co-stimulatory signalling region which is different to that of (b);
    (f) a transmembrane domain; and
    (g) a binding element that specifically interacts with a second epitope on a target antigen.

The applicants have found that the efficacy of this system is good and in particular may be better than that achieved using conventional third generation CARs having similar elements. Constructs of the type of the invention may be called 'parallel chimeric activating receptors' or 'pCAR'.

In addition, the proliferation of the cells, their ability to maintain their cytotoxic potency and to release IL-2 is maintained over many repeated rounds of stimulation with antigen-expressing tumour cells.

Without being bound by theory, the arrangement of the elements in the pCARs may be facilitating activity. For example, by definition, one of the co-stimulatory modules in a 3rd generation CAR must be placed away from its natural location close to the inner leaflet of the plasma membrane. This may cause it not to signal normally owing to impaired access to obligate membrane-associated partner molecules. Alternatively, close proximity of 2 co-stimulatory signalling modules in a 3rd generation CAR might lead to steric issues, preventing full engagement of one or more downstream signalling pathways. Both of these issues are avoided in the arrangement of the invention. Both the signalling moieties (b) and (e) may be fused directly to a transmembrane domain, ensuring that they are both adjacent to the plasma membrane within the cell. Furthermore, they may be spaced at distinct sites within the cell so that will not interact sterically with each other.

Suitable immuno-responsive cells for use in the first aspect of the invention include T-cells such as cytotoxic T-cells, helper T-cells or regulatory T-cells and Natural Killer (NK) cells. In particular, the immuno-responsive cell is a T-cell.

Suitable elements (a) above may include any suitable signalling region, including any region comprising an Immune-receptor-Tyrosine-based-Activation-Motif (ITAM), as reviewed for example by Love et al. Cold Spring Harbor Perspect. Biol 2010 2(6)|a002485. In a particular embodiment, the signalling region comprises the intracellular domain of human CD3 [zeta] chain as described for example in U.S. Pat. No. 7,446,190, or a variant thereof.

In particular, this comprises the domain, which spans amino acid residues 52-163 of the full-length human CD3 zeta chain. It has a number of polymorphic forms (e.g. Sequence ID: gb|AAF34793.1 and gb|AAA60394.1), which are shown respectively as SEQ ID NO 1 and 2:

```
                                              (SEQ ID NO 1)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR (SEQ ID NO 2)
RVKFSRSAEPPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

As used herein, the term 'variant' refers to a polypeptide sequence which is a naturally occurring polymorphic form of the basic sequence as well as synthetic variants, in which one or more amino acids within the chain are inserted, removed or replaced. However, the variant produces a biological effect which is similar to that of the basic sequence. For example, the variant mentioned above will act in a manner similar to that of the intracellular domain of human CD3 [zeta] chain. Amino acid substitutions may be regarded as "conservative" where an amino acid is replaced with a different amino acid in the same class with broadly similar properties. Non-conservative substitutions are where amino acids are replaced with amino acids of a different type or class.

Amino acid classes are defined as follows:

| Class | Amino acid examples |
| --- | --- |
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions may also be possible provided that these do not interrupt the function of the polypeptide as described above. Broadly speaking, fewer non-conservative substitutions will be possible without altering the biological activity of the polypeptides.

In general, variants will have amino acid sequences that will be at least 70%, for instance at least 71%, 75%, 79%, 81%, 84%, 87%, 90%, 93%, 95%, 96% or 98% Identical to the basic sequence, for example SEQ ID NO 1 or SEQ ID NO 2. Identity in this context may be determined using the BLASTP computer program with SEQ ID NO 2 or a fragment, in particular a fragment as described below, as the base sequence. The BLAST software is publicly available.

The co-stimulatory signal sequence (b) is suitably located between the transmembrane domain (c) and the signalling region (a) and remote from the binding element (d). Similarly the co-stimulatory signal sequence (e) is suitably located adjacent the transmembrane domain (f) and remote from the binding element (g).

Suitable co-stimulatory signalling regions for use as elements (b) and (e) above are also well known in the art, and include members of the B7/CD28 family such as B7-1, B7-2, B7-H1, B7-H2, B7-H3, B7-H4, B7-H6, B7-H7, BTLA, CD28, CTLA-4, Gi24, ICOS, PD-1, PD-L2 or PDCD6; or ILT/CD85 family proteins such as LILRA3, LILRA4, LILRB1, LILRB2, LILRB3 or LILRB4; or tumour necrosis factor (TNF) superfamily members such as 4-1BB, BAFF, BAFF R, CD27, CD30, CD40, DR3, GITR, HVEM, LIGHT, Lymphotoxin-alpha, OX40, RELT, TACI, TL1A, TNF-alpha or TNF RII; or members of the SLAM family such as 2B4, BLAME, CD2, CD2F-10, CD48, CD8, CD84, CD229, CRACC, NTB-A or SLAM; or members of the TIM family such as TIM-1, TIM-3 or TIM-4; or other co-stimulatory molecules such as CD7, CD96, CD160, CD200, CD300a, CRTAM, DAP12, Dectin-1, DPPIV, EphB6, Integrin alpha 4 beta 1, Integrin alpha 4 beta 7/LPAM-1, LAG-3 or TSLP R.

The selection of the co-stimulatory signalling regions may be selected depending upon the particular use intended for the transformed cells. In particular, the co-stimulatory signalling regions selected for (b) and (e) above are those which may work co-operatively or synergistically together. For example, the co-stimulatory signalling regions for (b) and (e) may be selected from CD28, CD27, ICOS, 4-1BB, OX40, CD30, GITR, HVEM, DR3 or CD40.

In a particular embodiment, one of (b) or (e) is CD28 and the other is 4-1BB or OX40.

In a particular embodiment, (b) is CD28.

In another particular embodiment (e) is 4-1BB or OX40 and in particular, is 4-1BB. In another embodiment, (e) is CD27.

The transmembrane domains of (c) and (f) above may be the same or different but in particular are different to ensure separation of the constructs on the surface of the cell. Selection of different transmembrane domains may also enhance stability of the vector since inclusion of a direct repeat nucleic acid sequence in the viral vector renders it prone to rearrangement, with deletion of sequences between the direct repeats. Where the transmembrane domains of (c) and (f) are the same however, this risk can be reduced by modifying or "wobbling" the codons selected to encode the same protein sequence.

Suitable transmembrane domains are known in the art and include for example, CD8a, CD28, CD4 or CD3z transmembrane domains.

Where the co-stimulatory signalling region comprises CD28 as described above, the CD28 transmembrane domain represents a suitable option. The full length CD28 protein is a 220 amino acid protein of SEQ ID NO 3.

```
                                           (SEQ ID NO 3)
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPGP

TRKHYQPYAPPRDFAAYRS
``` where the transmembrane domain is shown in bold type.

In particular, one of the co-stimulatory signalling regions is based upon the hinge region and suitably also the transmembrane domain and endodomain of CD28. In particular, which comprises amino acids 114-220 of SEQ ID NO 3, shown below as SEQ ID NO 4.

```
                                           (SEQ ID NO 4)
IEVMYPPPYLDNEKSNGTIIHVKGKHLCPSPLFPGPSKPWVLVVVGGVLA

CYSLLVTVAFIIFWVRSKRSRLLHSDYMNMTPRRPGPTRKHYQPYAPPRD

FAAYRS
```

In a particular embodiment, one of the co-stimulatory signalling regions (b) or (e) above is a modified form of SEQ ID NO 4 which includes a c-myc tag of SEQ ID No 5.

The c-myc tag is well known and is of SEQ ID NO 5.

```
                                           (SEQ ID NO 5)
EQKLISEEDL
```

The c-myc tag may be added to the co-stimulatory signalling region (b) or (e) by insertion into the ectodomain or by replacement of a region in the ectodomain, which is therefore within the region of amino acids 1-152 of SEQ ID NO 3.

In a particularly preferred embodiment, the c-myc tag replaces MYPPPY motif in the CD28 sequence. This motif represents a potentially hazardous sequence. It is responsible for interactions between CD28 and its natural ligands, CD80 and CD86, so that it provides potential for off-target toxicity when CAR T-cells encounter a target cell that expresses either of these ligands. By replacement of this motif with a tag sequence as described above, the potential for unwanted side effects is reduced.

Thus in a particular embodiment, the co-stimulatory signalling region (b) of the construct is of SEQ ID NO 6.

```
                                           (SEQ ID NO 6)
IEVEQKLISEEDLLDNEKSNGTIIHVKGKHLCPSPLFPGPSKPFWVLVVV

GGVLACYSLLVTVAFIIFWVRSKRSRLLHSDYMNMTPRRPGPTRKHYQPY

APPRDFAAYRS
```

Furthermore, the inclusion of a c-myc epitope means that detection of the CAR T-cells using a monoclonal antibody is facilitated. This is very useful since flow cytometric detection had proven unreliable when using some available antibodies.

In addition, the provision of a c-myc epitope tag could facilitate the antigen independent expansion of targeted CAR T-cells, for example by cross-linking of the CAR using the appropriate monoclonal antibody, either in solution or immobilised onto a solid phase (e.g. a bag).

Moreover, expression of the epitope for the anti-human c-myc antibody, 9e10, within the variable region of a TCR has previously been shown to be sufficient to enable antibody-mediated and complement mediated cytotoxicity both in vitro and in vivo (Kieback et al. (2008) Proc. Natl. Acad. Sci. USA, 105(2) 623-8). Thus, the provision of such epitope tags could also be used as a "suicide system", whereby an antibody could be used to deplete CAR T-cells in vivo, in the event of toxicity.

The binding elements (d) and (g) will be different and will bind the same, overlapping or different epitopes. In a particular embodiment the first and second epitopes are associated with the same receptor or antigen. Thus the first and second epitopes as described above may, in some cases, be the same, or overlapping so that the binding elements (d) and (g) will compete in their binding. Alternatively, the first and second epitopes may be different and associated with the same or different antigens depending upon the particular therapy being envisaged. In one embodiment, the antigens are different but may be associated with the same disease such as the same specific cancer.

As used herein, the term 'antigen' refers to any member of a specific binding pair that will bind to the binding elements. Thus the term includes receptors on target cells.

Thus suitable binding elements (d) and (g) may be any element which provides the pCAR with the ability to recognize a target of interest. The target to which the pCARs of the invention are directed can be any target of clinical interest to which it would be desirable to induce a T cell response. This would include markers associated with cancers of various types, including for example, one or more ErbB receptors or the $\alpha_v\beta_6$ integrin, markers associated with prostate cancer (for example using a binding element that binds to prostate-specific membrane antigen (PSMA)), breast cancer (for example using a binding element that targets Her-2 (also known as ErbB2)) and neuroblastomas (for example using a binding element that targets GD2), melanomas, small cell or non-small cell lung carcinoma, sarcomas and brain tumours. In a particular embodiment, the target is one or more ErbB dimers as described above or the receptor for colony stimulating factor-1 (CSF-1R) or the $\alpha_v\beta_6$ integrin, all of which have been implicated in several solid tumours.

The binding elements used in the pCARs of the invention may comprise antibodies that recognize a selected target. For convenience, the antibody used as the binding element is preferably a single chain antibody (scFv) or single domain antibody, from a camelid, human or other species. Single chain antibodies may be cloned from the V region genes of a hybridoma specific for a desired target. The production of such hybridomas has become routine, and the procedure will not be repeated here. A technique which can be used for cloning the variable region heavy chain (VH) and variable region light chain (VL) has been described in Orlandi et al., Proc. Natl Acad. Sci. (USA) 86: 3833-3837 (1989). Briefly, mRNA is isolated from the hybridoma cell line, and reverse transcribed into complementary DNA (cDNA), for example using a reverse transcriptase polymerase chain reaction (RT-PCR) kit. Sequence-specific primers corresponding to the sequence of the VH and VL genes are used. Sequence analysis of the cloned products and comparison to the known sequence for the VH and VL genes can be used to show that the cloned VH gene matched expectations. The VH and VL genes are then attached together, for example using an oligonucleotide encoding a (gly4-ser)3 linker.

Alternatively, a binding element of a pCAR may comprise ligands such as the T1E peptide (binds ErbB homo- and heterodimers), colony-stimulating factor-1 (CSF-1) or IL-34 (both bind to the CSF-1 receptor). The T1E peptide is a chimeric fusion protein composed of the entire mature human EGF protein, excluding the five most N-terminal amino acids (amino acids 971-975 of pro-epidermal growth factor precursor (NP_001954.2)), which have been replaced by the seven most N-terminal amino acids of the mature human TGF-α protein (amino acids 40-46 of pro-transforming growth factor alpha isoform 1 (NP_003227.1)).

In another embodiment, a binding element of a pCAR comprises an $\alpha_v\beta_6$ integrin-specific binding agent. The integrin $\alpha_v\beta_6$ is now regarded as a target in cancer as it has been found to be strongly upregulated in many types of cancer. $\alpha_v\beta_6$ has been identified as a receptor for foot-and-mouth disease virus (FMDV) in vitro by binding through an RGD motif in the viral capsid protein, VP1. As a result, as described for example in U.S. Pat. No. 8,383,593, a range of peptides derived from FMDV and in particular, peptides originating from the VP1 protein of FMDV and comprising an RGD motif showed increased binding potency and binding specificity. In particular, these peptides comprise the sequence motif

RGDLX$^5$X$^6$L (SEQ ID NO 7)

or

RGDLX$^5$X$^6$I, (SEQ ID NO 8)

wherein LX$^5$X$^6$L or LX$^5$X$^6$I is contained within an alpha helical structure, wherein X$^5$ and X$^6$ are helix promoting residues, which have a conformational preference greater than 1.0 for being found in the middle of an [alpha]-helix (from Creighton, 1993 and Pace C. N. and Scholtz J. M. (1998), Biophysical Journal, Vol. 75, pages 422-427). In particular such residues are independently selected from the group consisting of Glu, Ala, Leu, Met, Gin, Lys, Arg, Val, lie, Trp, Phe and Asp.

Specific examples of such sequences include SEQ ID Nos 9-11 or variants thereof:

YTASARGDLAHLTTTHARHL (SEQ ID NO 9)

GFTTGRRGDLATIHGMNRPF (SEQ ID NO 10)

or

NAVPNLRGDLQVLAQKVART (SEQ ID NO 11)

These peptides may form a particular group of binding elements for the CARs of the present application.

For selected malignancies such as Hodgkin's lymphoma and some breast cancers, two natural ligands are CSF-1 and IL-34 and these form particularly suitable binding elements for (d) and (g). They do however bind with different affinities. The affinity of binding can impact on the activity observed. It may be beneficial in this case to ensure that the binding element with the lower binding affinity is used as binding element (d) and that with the higher binding affinity is used as binding element (g). In particular, in an embodiment, the relative affinity of the second generation CAR (i) for its cognate target is lower than that of the partnering TNFR-based chimeric co-stimulatory receptor (ii). This does not preclude the use of high or low affinity targeting moieties in each position provided that this relative affinity relationship is maintained. Thus in the case of the present invention, in a particular embodiment, binding element (d) is CSF-1 which has a relatively low binding affinity, whilst binding element (g) comprises IL-34 which has a higher binding affinity.

Suitably the binding element is associated with a leader sequence which facilitates expression on the cell surface. Many leader sequences are known in the art, and these include the macrophage colony stimulating factor receptor (FMS) leader sequence or CD124 leader sequence.

In a further embodiment, the cells expressing the pCAR are engineered to co-express a chimeric cytokine receptor, in particular the 4αβ chimeric cytokine receptor. In 4αβ, the ectodomain of the IL-4 receptor-α chain is joined to the transmembrane and endodomains of IL-2/15 receptor-β. This allows the selective expansion and enrichment of the genetically engineered T-cells ex vivo by the culture of these cells in a suitable support medium, which, in the case of 44, would comprise IL-4 as the sole cytokine support. Similarly, the system can be used with a chimeric cytokine receptor in which the ectodomain of the IL-4 receptor-α chain is joined to the transmembrane and endodomains of another receptor that is naturally bound by a cytokine that also binds to the common γ chain.

As discussed, these cells are useful in therapy to stimulate a T-cell mediated immune response to a target cell population. Thus a second aspect of the invention provides a method for stimulating a T cell mediated immune response to a target cell population in a patient in need thereof, said method comprising administering to the patient a population of immuno-responsive cells as described above, wherein the binding elements (d) and (g) are specific for the target cell.

In a third aspect of the invention, there is provided a method for preparing an immuno-responsive cell according to any one of the preceding claims, said method comprising transducing a cell with a first nucleic acid encoding a CAR of structure (i) as defined above; and also a second nucleic acid encoding a CAR of structure (ii) as defined above.

In particular, in this method, lymphocytes from a patient are transduced with the nucleic acids encoding the CARs of (i) and (ii). In particular, T-cells are subjected to genetic modification, for example by retroviral mediated transduction, to introduce CAR coding nucleic acids into the host T-cell genome, thereby permitting stable CAR expression. They may then be reintroduced into the patient, optionally after expansion, to provide a beneficial therapeutic effect. Where the cells such as the T-cells are engineered to co-express a chimeric cytokine receptor such as 4αβ, the expansion step may include an ex vivo culture step in a medium which comprises the cytokine, such as a medium comprising IL-4 as the sole cytokine support in the case of 4αβ. Alternatively, the chimeric cytokine receptor may comprise the ectodomain of the IL-4 receptor-α chain joined to the endodomain used by a common γ cytokine with distinct properties, such as IL-7. In this setting, expansion of the cells in IL-4 may result in less cell differentiation, capitalizing on the natural ability of IL-7 to achieve this effect. In this way, selective expansion and enrichment of genetically engineered T-cells with the desired state of differentiation can be ensured.

In a fourth aspect of the invention, there is provided a combination of a first nucleic acid encoding a CAR of (i) above and a second nucleic acid encoding a CCR of (ii) above. As indicated previously, this combination is referred to as a pCAR. Suitable sequences for the nucleic acids will be apparent to a skilled person. The sequences may be optimized for use in the required immuno-responsive cell. However, in some cases, as discussed above, codons may be varied from the optimum or 'wobbled' in order to avoid repeat sequences. Particular examples of such nucleic acids will encode the preferred embodiments described above.

In order to achieve transduction, the nucleic acids of the fourth aspect of the invention are suitably introduced into a vector, such as a plasmid or a retroviral vector. Such vectors including plasmid vectors, or cell lines containing them form a further aspect of the invention.

The first and second nucleic acids or vectors containing them may be combined in a kit, which is supplied with a view to generating immuno-responsive cells of the first aspect of the invention in situ.

Parallel chimeric activating receptors (pCAR) encoded by the nucleic acids described above form a further aspect of the invention.

DETAILED DESCRIPTION OF THE INVENTION

The invention will now be particularly described by way of example and with reference to the following Figures in which:

FIG. 1A,B is a schematic diagram showing a panel of CARs and pCARs (named C34B and 34CB) embodying the invention. All CARs and pCARs were co-expressed in the SFG retroviral vector with 4αβ, a chimeric cytokine receptor in which the IL-4 receptor-α ectodomain has been fused to the transmembrane and endodomain of IL-2 receptor-β. Use of 4αβ allows selective enrichment and expansion of gene-modified T-cells by culture in IL-4, since it recruits the gamma c (γc) chain.

FIG. 2A,B shows the results of an experiment using CARs shown in FIG. 1A,B. T-cells ($1\times10^6$ cells) expressing these CARs and pCARs (or untransduced (UT) as control) were co-cultivated in vitro for 24 hours with T47D tumour cells that express (T47D-FMS) or lack (T47D) the cognate target antigen (Colony-stimulating factor-1 receptor (CSF-1R), encoded by c-fms). Residual viable tumour cells were then quantified by MTT assay.

Figure 7A:
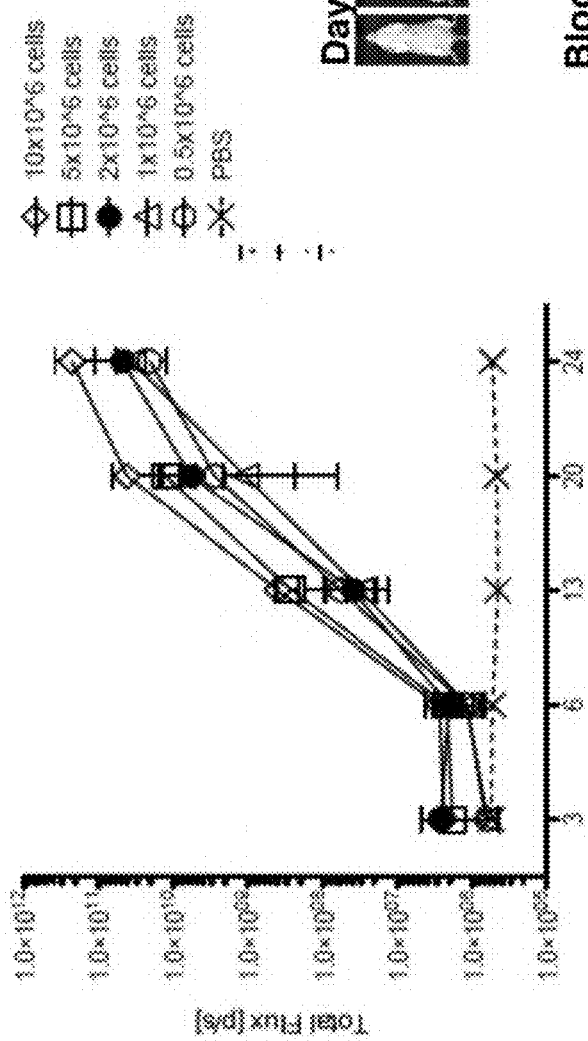
Figure 7B:
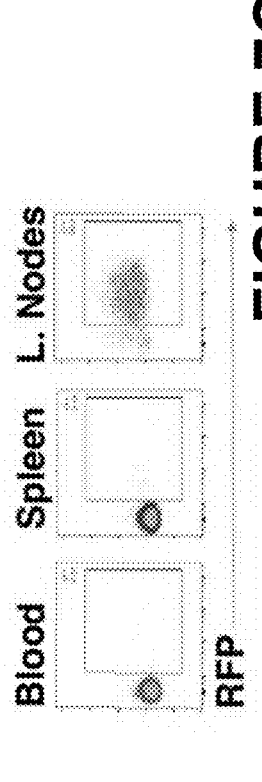
Figure 7C:
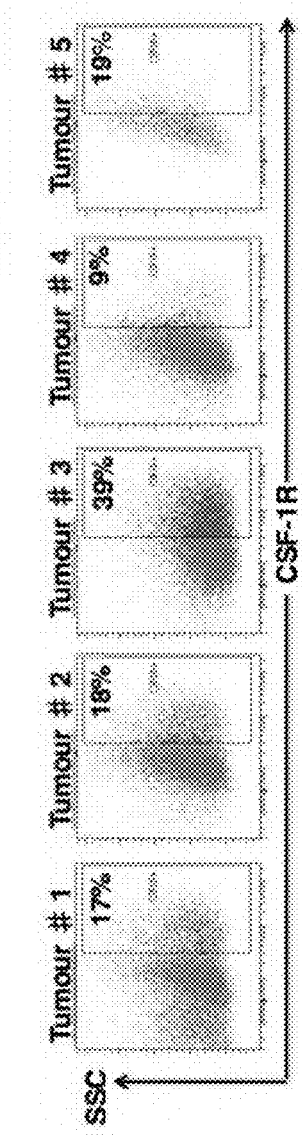
Figure 7D:
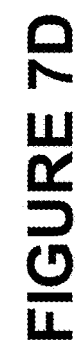

FIG. 7A-D demonstrates the establishment of an in vivo xenograft model of CSF-1R-expressing anaplastic large cell lymphoma, which allowed subsequent testing of anti-tumour activity of CAR and pCAR-engineered T-cells. The model was established using K299 cells, engineered to express firefly luciferase (luc) and red fluorescent protein (RFP). FIG. 7A shows tumour formation following the intravenous injection of the indicated doses of K299 luc cells, quantified by bioluminescence imaging (BLI). Representative BLI images are shown in FIG. 7B in mice that received 2 million tumour cells. Expression of $RFP^+$ tumour cells (FIG. 7C) in the indicated tissues are shown, demonstrating that tumours only formed in lymph nodes in this model. Expression of the CSF-1R on five representative lymph node tumours is shown in FIG. 7D.

Figure 8A:
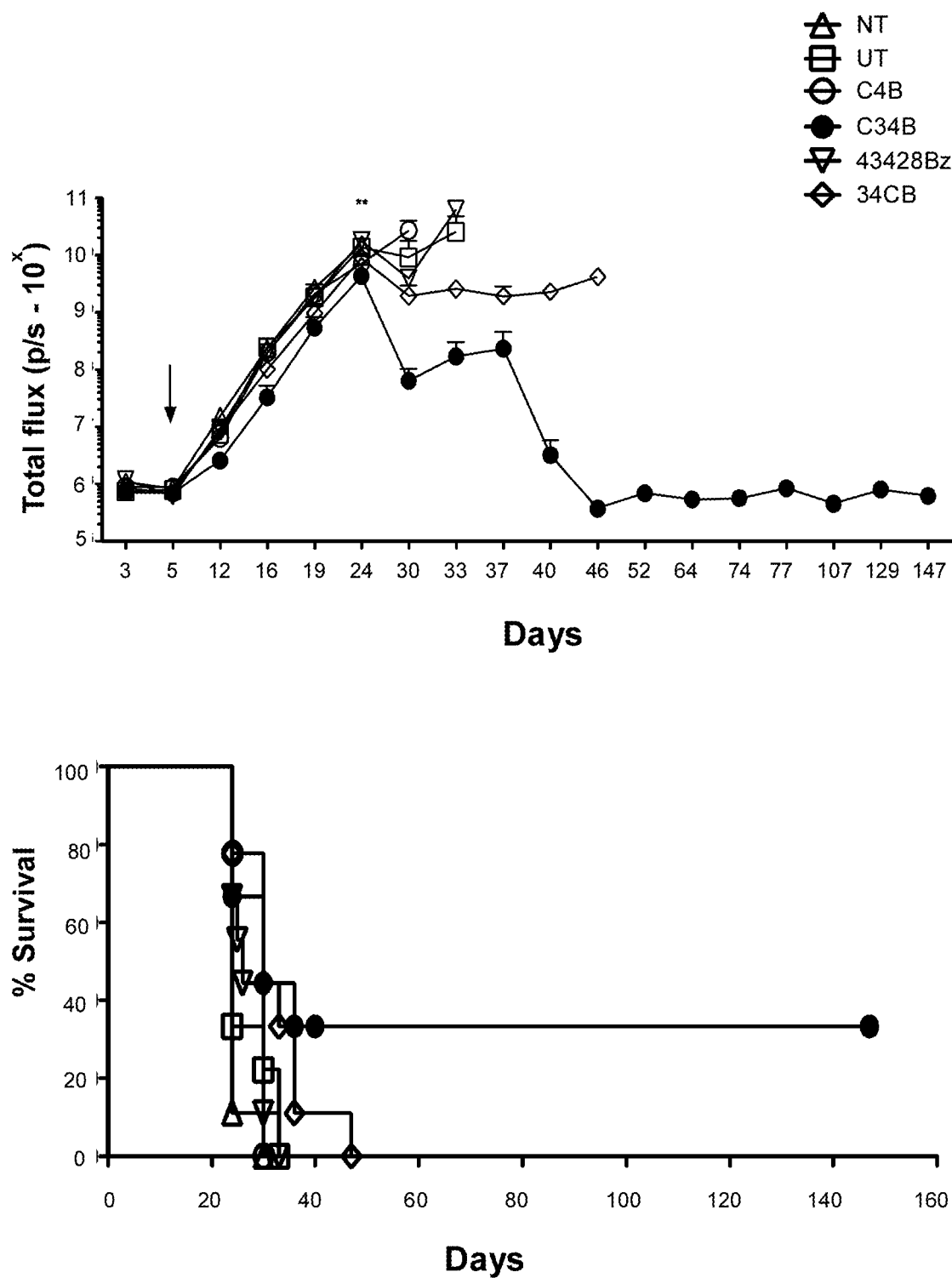
Figure 8B:
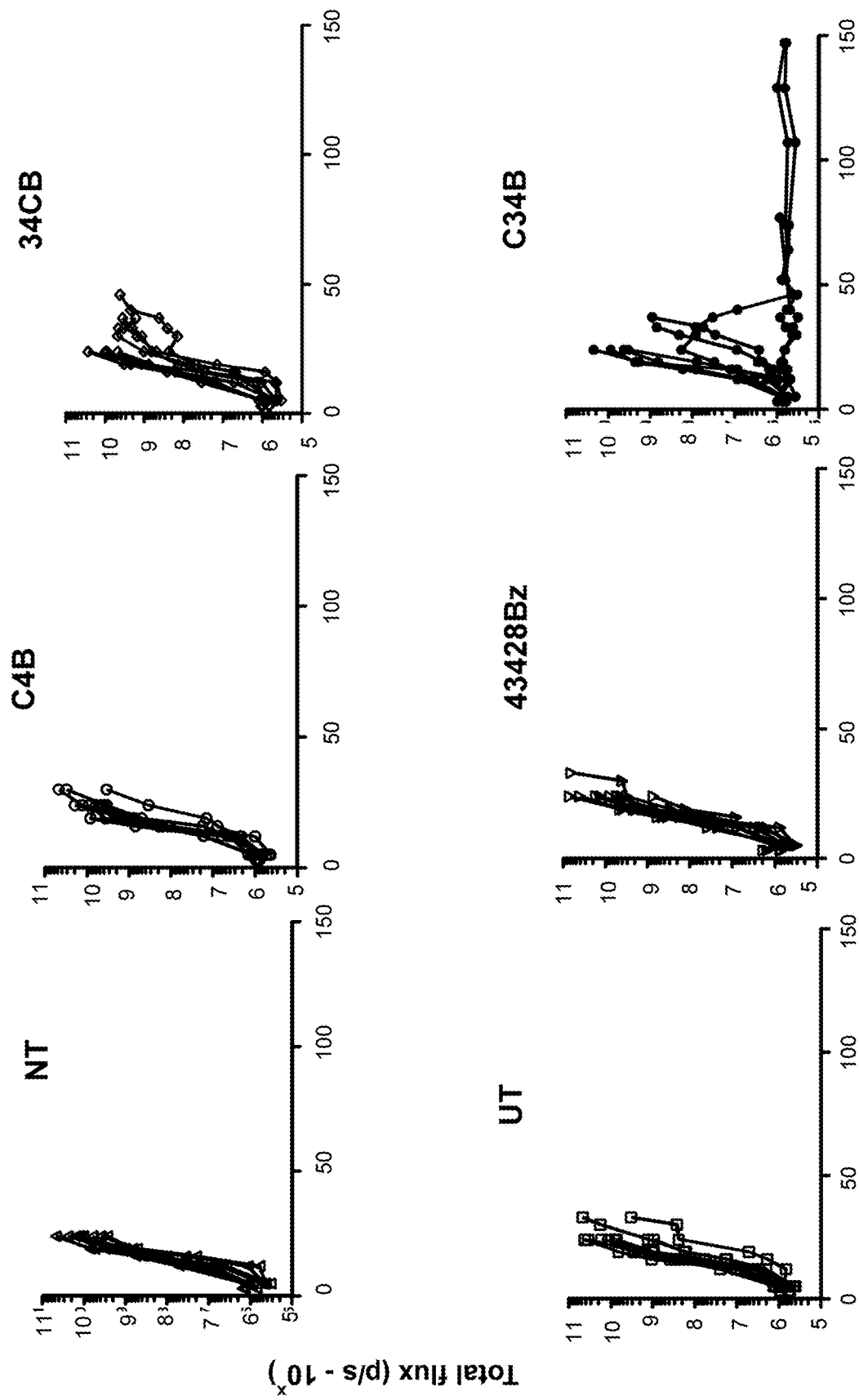

FIG. 8A,B shows the results of therapeutic studies in which K299 luc cells were injected intravenously in SCID Beige mice (n=9 per group, divided over 2 separate experiments). After 5 days, mice were treated with CAR T-cells. Pooled bioluminescence emission from tumours is shown in FIG. 8A. Bioluminescence emission from individual mice is shown in FIG. 8B and survival of mice shown in FIG. 8A.

Figure 9:
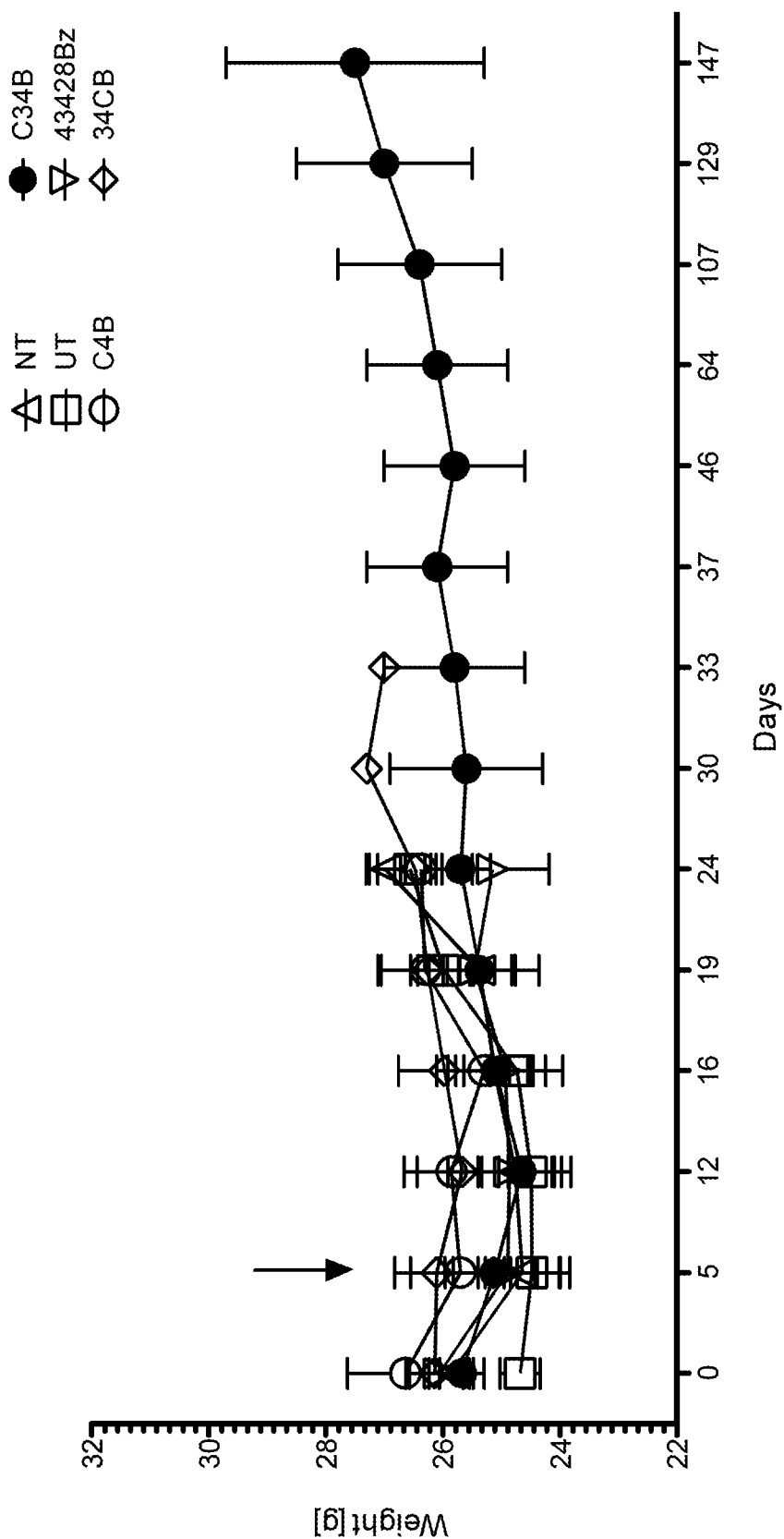

FIG. 9 shows the weights of animals used in the therapeutic study over time.

Figure 10:
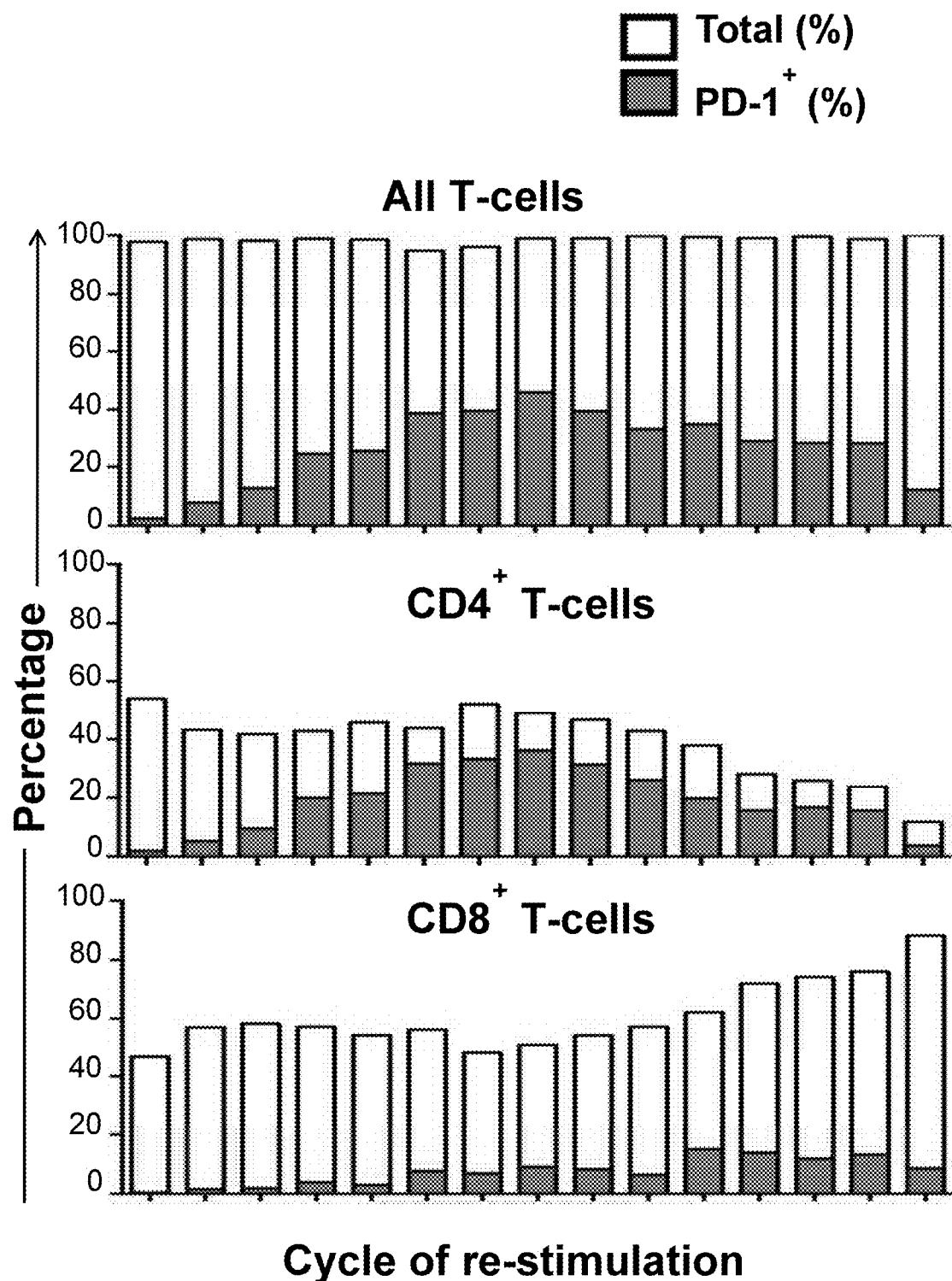
Figure 11:
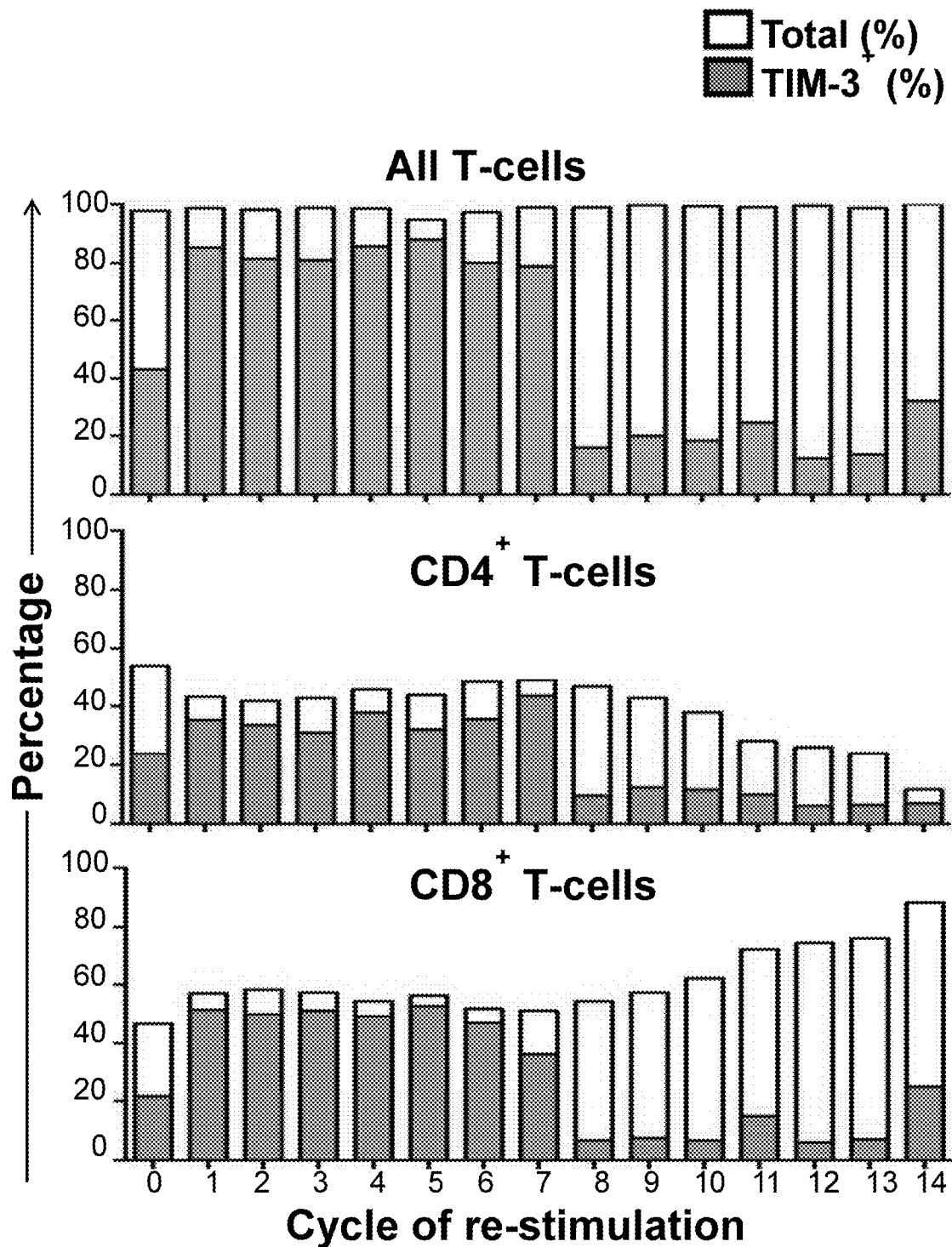
Figure 12:
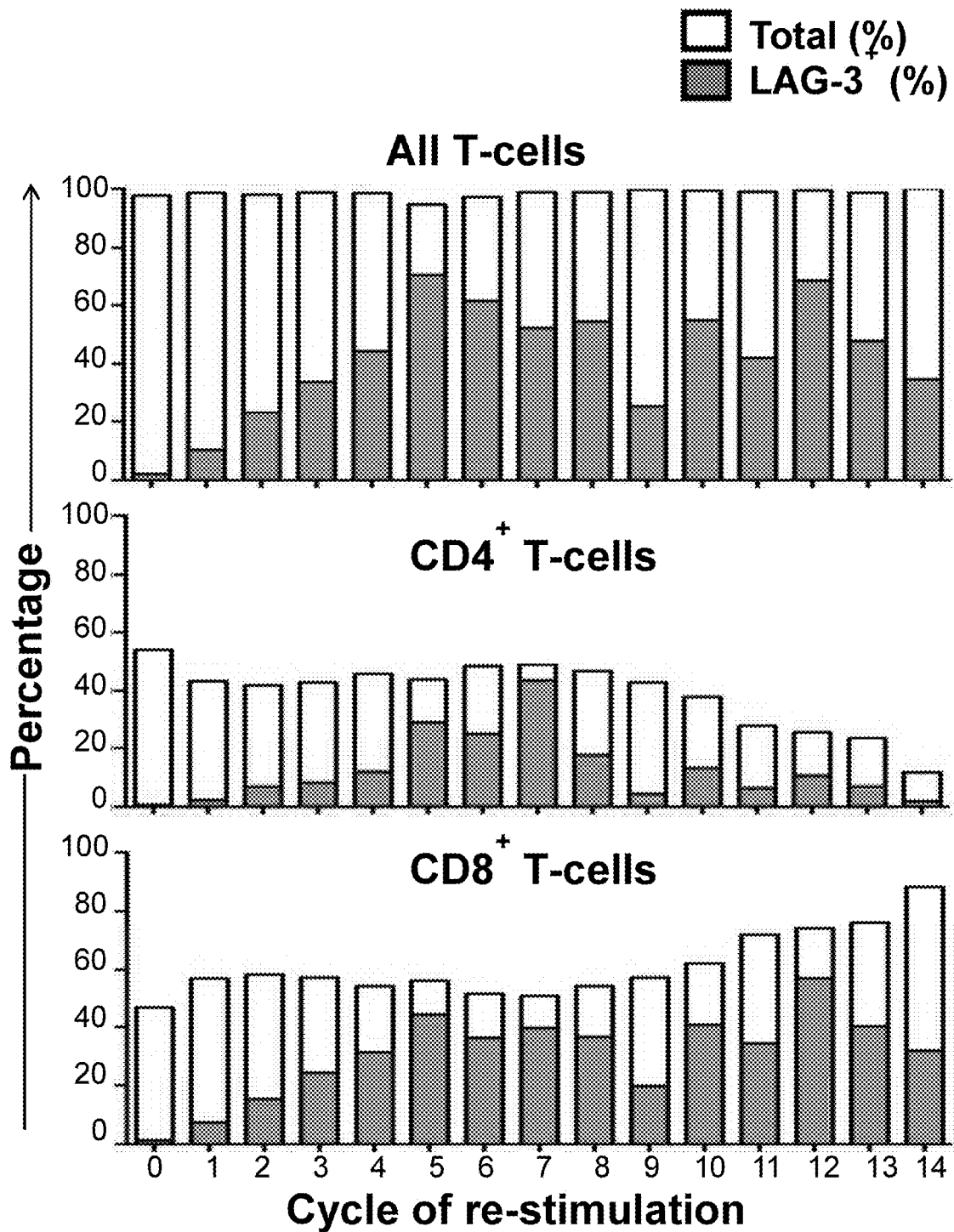
Figure 13:
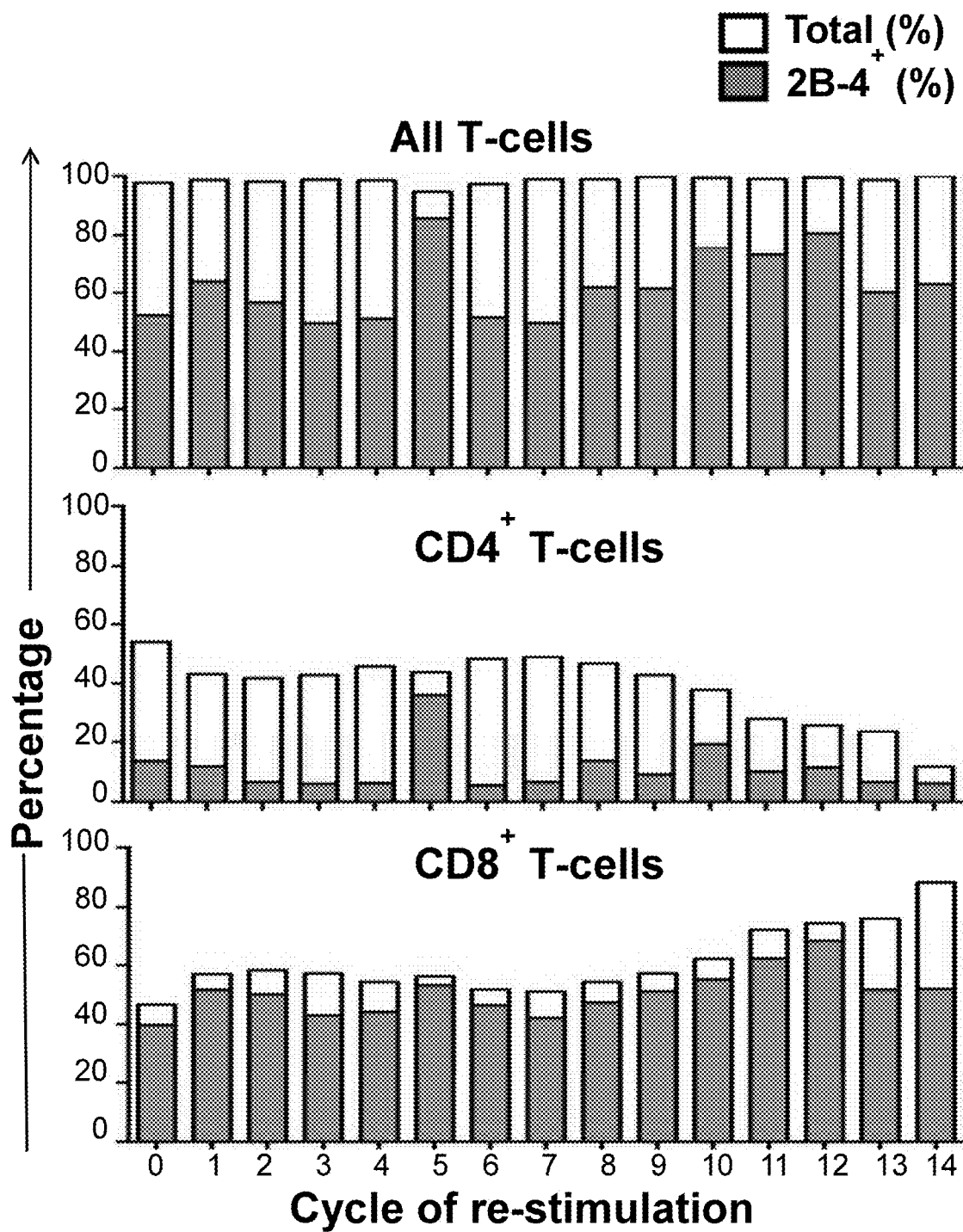

FIGS. 10-13 show the results of analysis of the expression of 'exhaustion markers' from dual CAR (C34B) expressing T-cells of the invention where FIG. 10 shows the results for PD1 analysis, FIG. 11 shows the results for TIM3 analysis, FIG. 12 shows the results of LAG3 analysis and FIG. 13 shows the results for 2B4 analysis.

Figure 14:
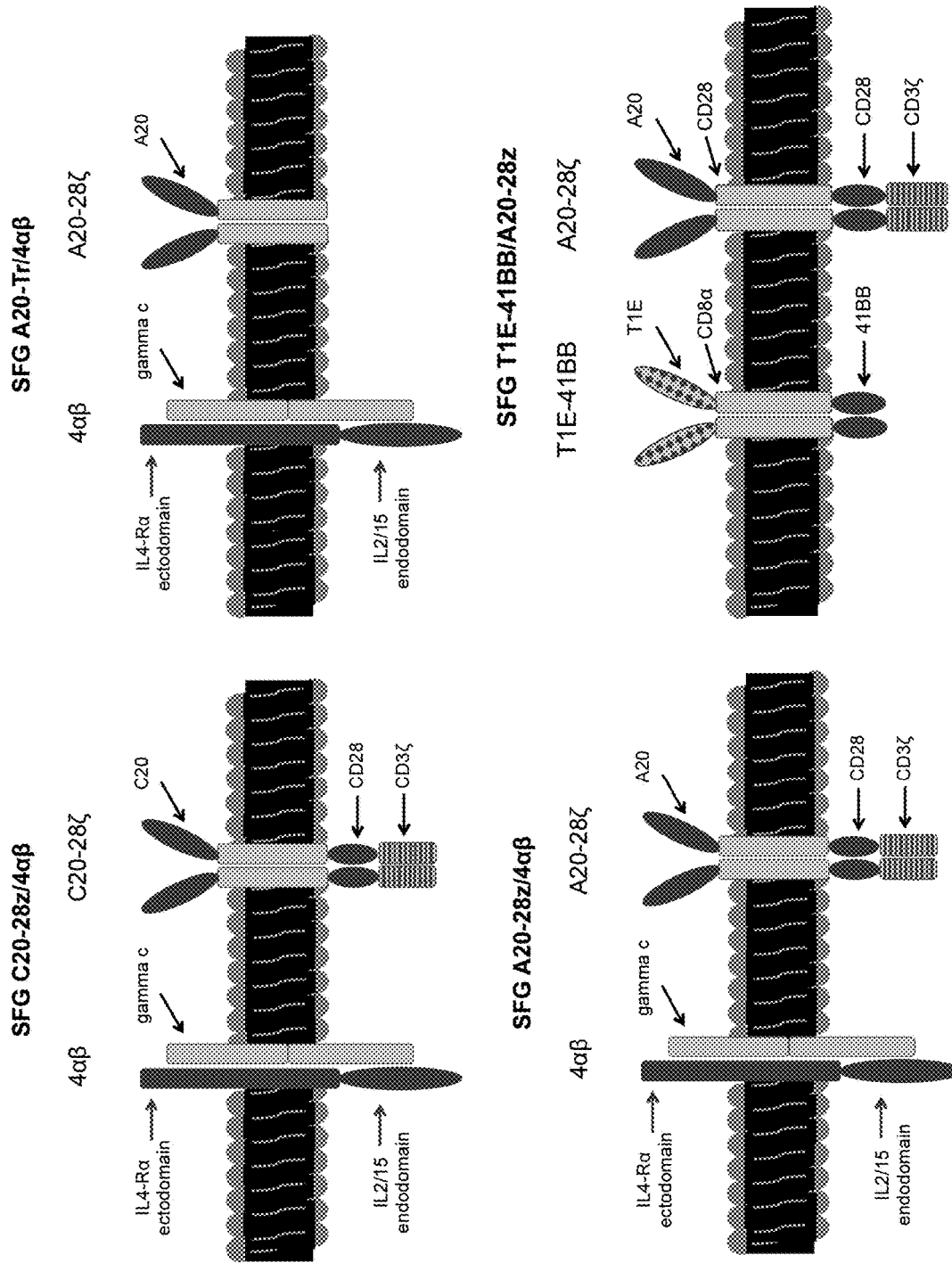

FIG. 14 is a schematic diagram of a panel of CARs and constructs targeted to the integrin αvβ6 which have been prepared including a pCAR (named SFG TIE-41BB/A20-28z) embodying the invention. A20-28z is a second generation CAR that is targeted using the A20 peptide derived from foot and mouth disease virus. A20 binds with high affinity to αvβ6 and with 85-1000 fold lower affinity to other RGD-binding integrins. C20-28z is a matched control in which key elements of A20 have been mutated to abrogate integrin binding activity. All CARs have been co-expressed with 4αβ as described in FIG. 1A,B.

Figure 15A:
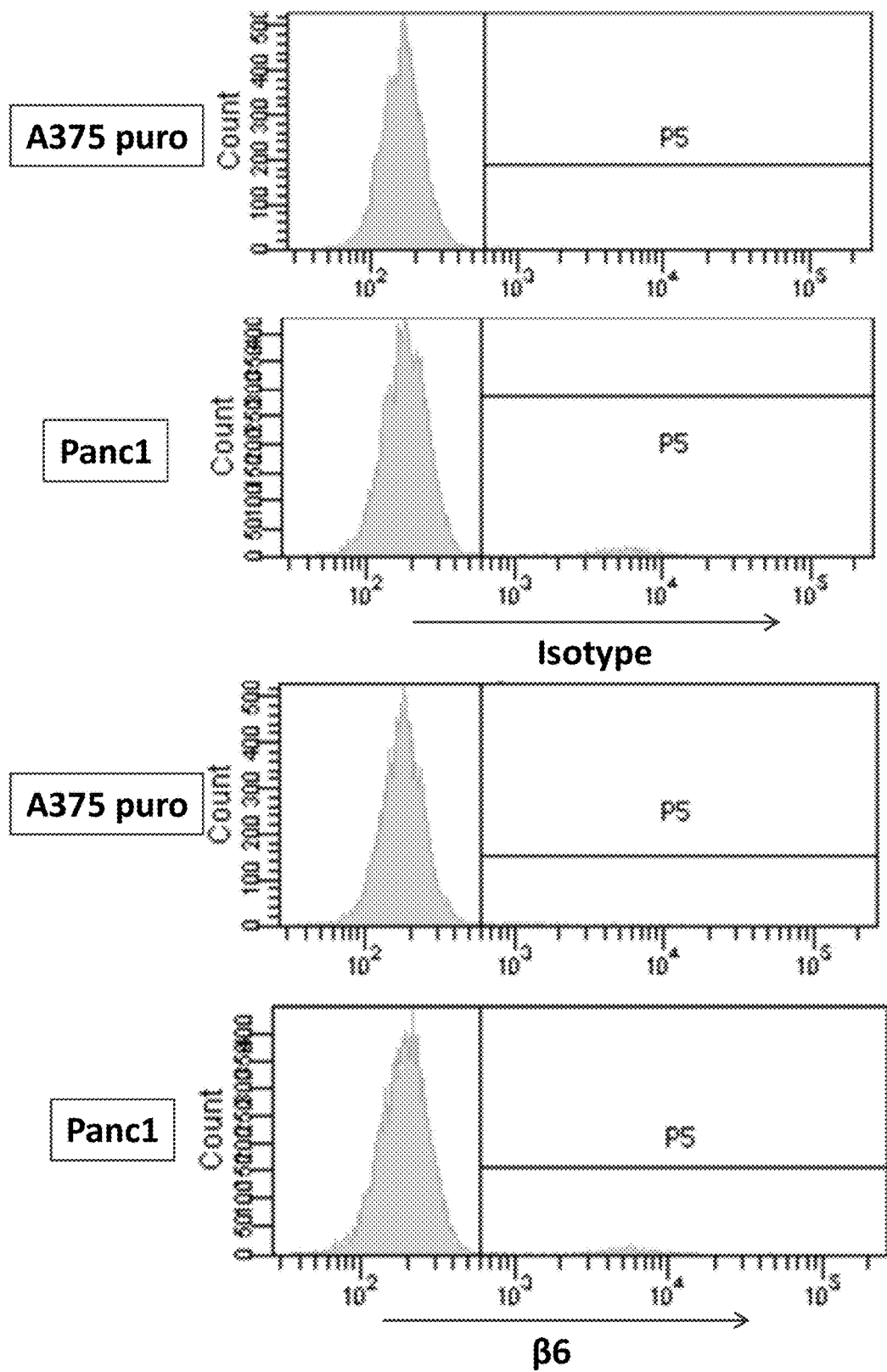
Figure 15B:
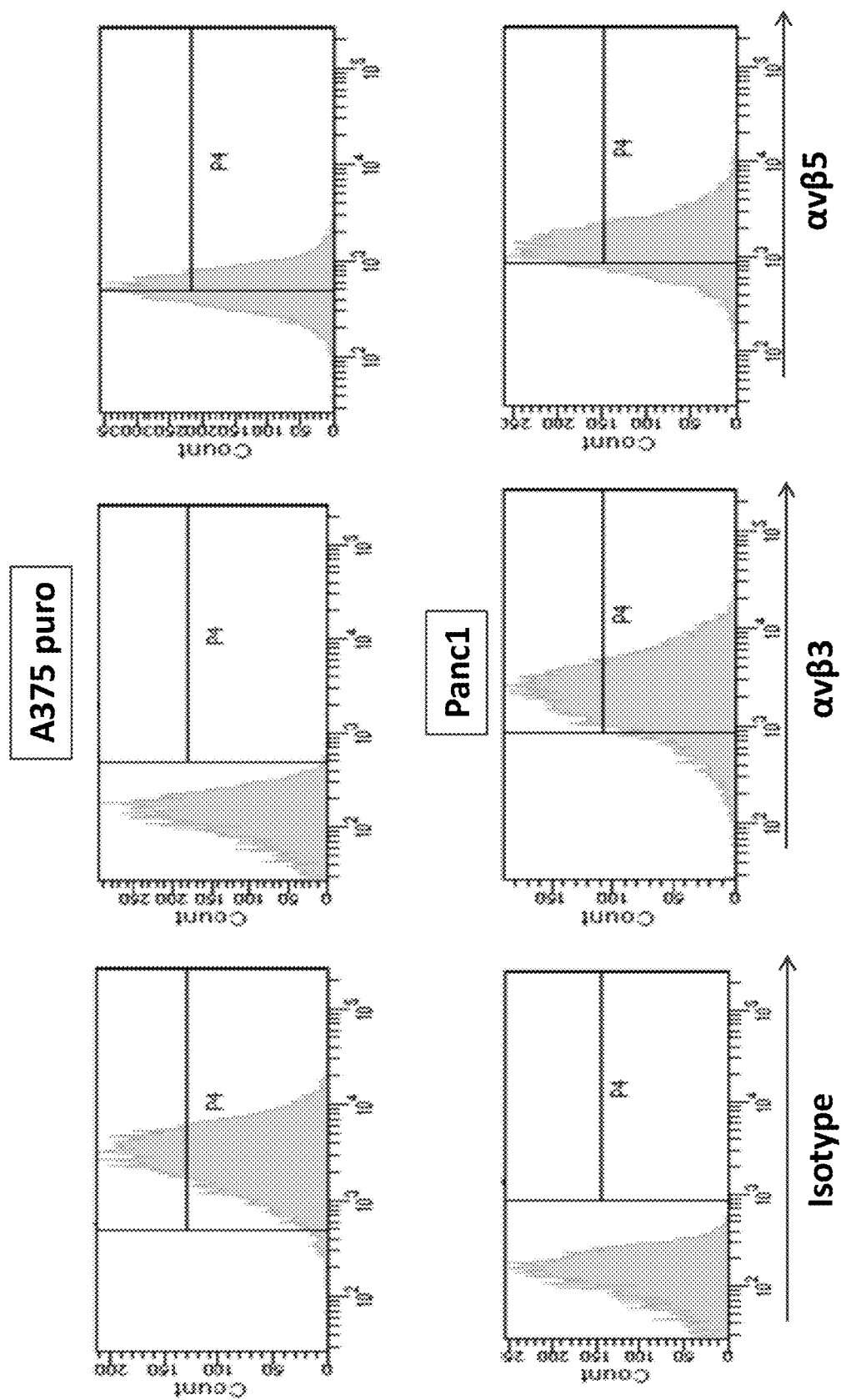

FIG. 15A,B is a series of histograms obtained by flow cytometry illustrating integrin expression in A375 puro and Panc1 cells. Cells were stained with anti-β6 (Biogen Idec) followed by secondary anti-mouse PE, anti-αvβ3 or anti- αvβ5 (both APC conjugated, Bio-Techne). Gates were set based on secondary antibody alone or isotype controls.

Figure 16A:
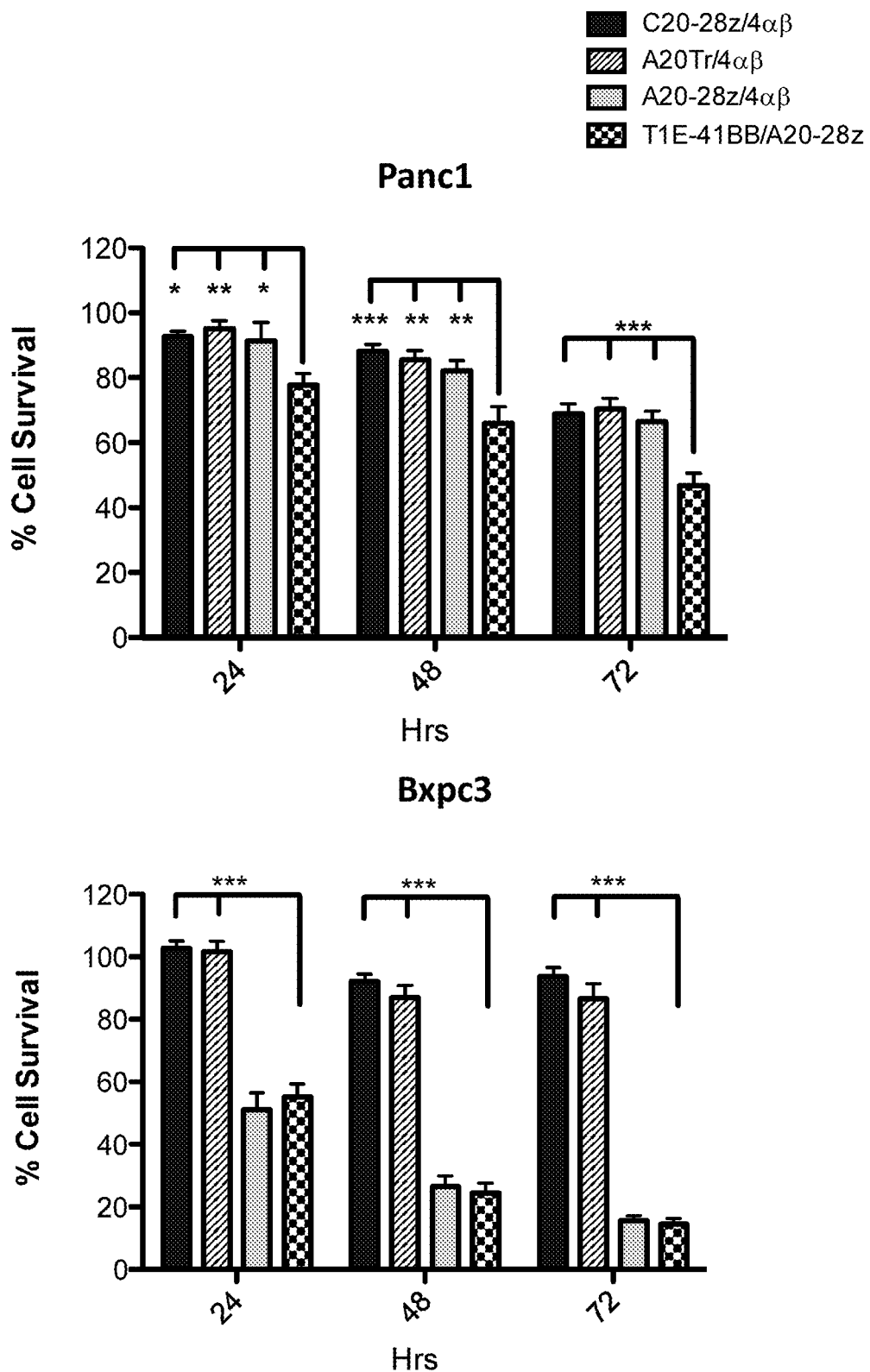
Figure 16B:
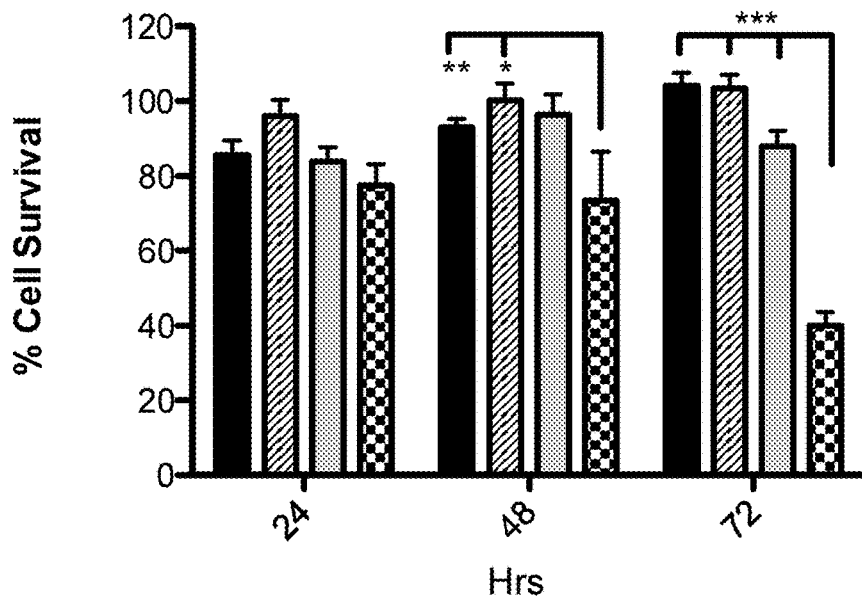
Figure 16B:
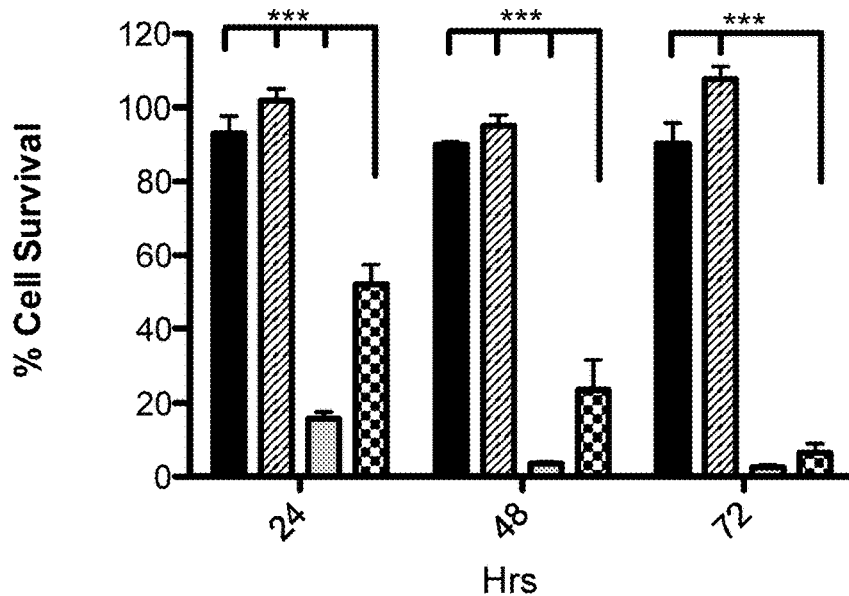

FIG. 16A,B is a series of graphs illustrating the cytotoxicity of CARs Including the pCARs of the invention targeted to αvβ6. T-cells expressing the indicated CARs and pCARs were co-cultivated with αvβ6-negative (Panc1 and A375 puro) or αvβ6-positive (Bxpc3 and A375 puro 06) tumour cells. Data show the mean±SEM of 2-7 independent experiments, each performed in triplicate. $*p<0.05$; $p<0.01$; $*p<0.001$.

Figure 17A:
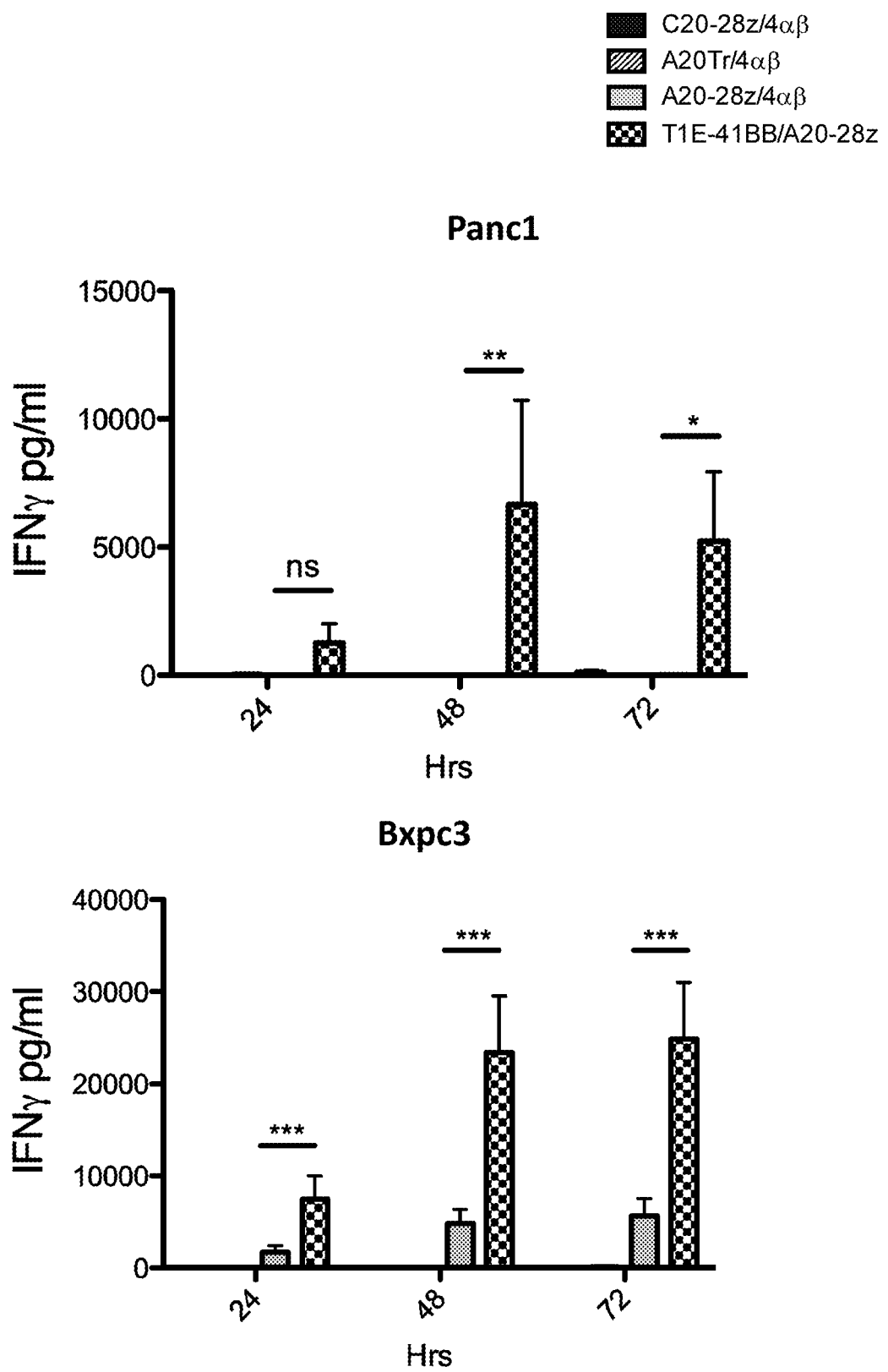
Figure 17B:
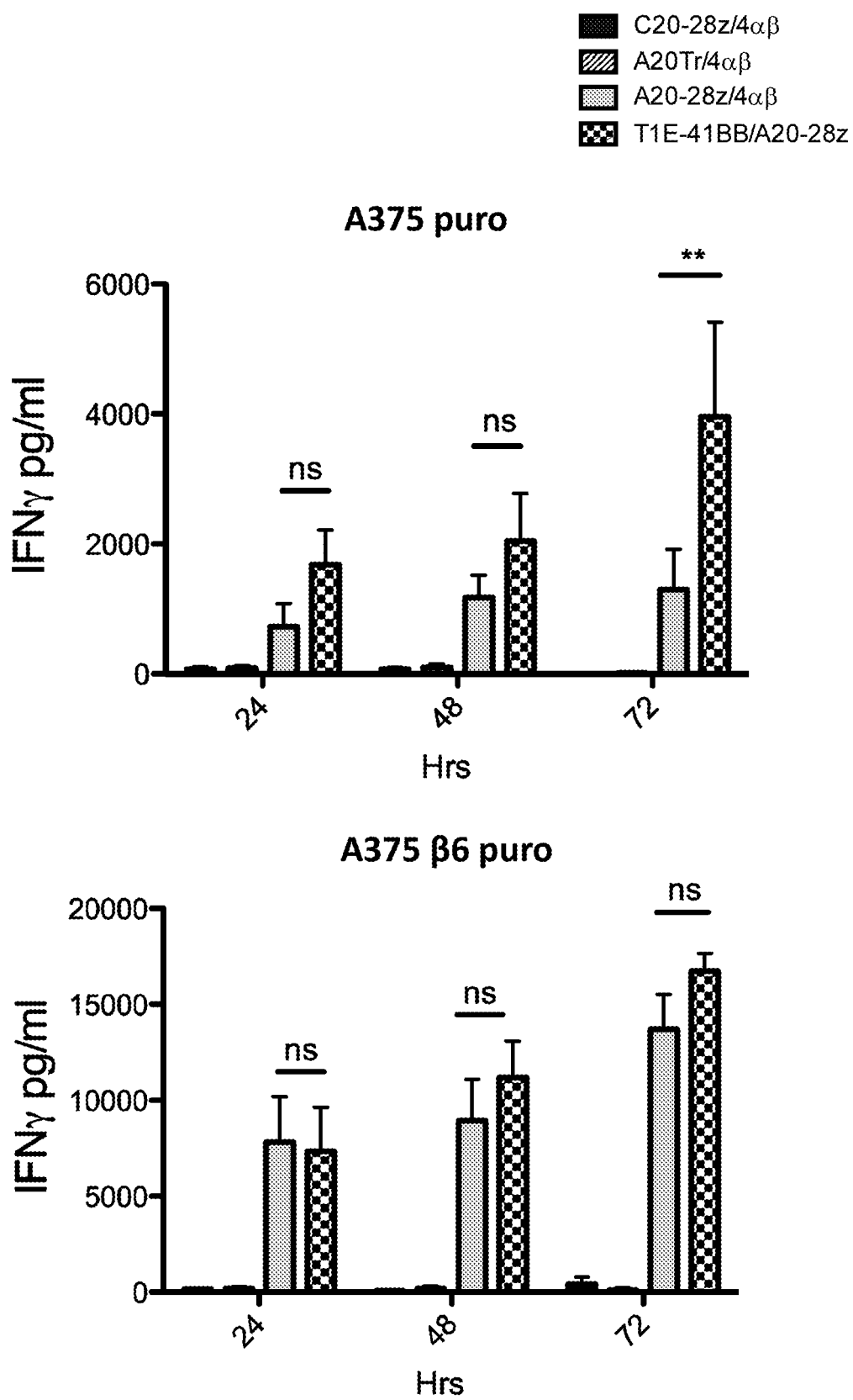

FIG. 17A,B is a series of graphs showing production of IFN-γ by CARs including pCARs of the invention, targeted to αvβ6. T-cells expressing the indicated CARs and pCARs were co-cultivated with αvβ6-negative (Panc1 and A375 puro) or αvβ6-positive (Bxpc3 and A375 puro 06) tumour cells. Data show the mean t SEM of 5-6 Independent experiments, each performed in duplicate. $*p<0.05$; $p<0.01$; $*p<0.001$; ns—not significant.

Figure 18A:
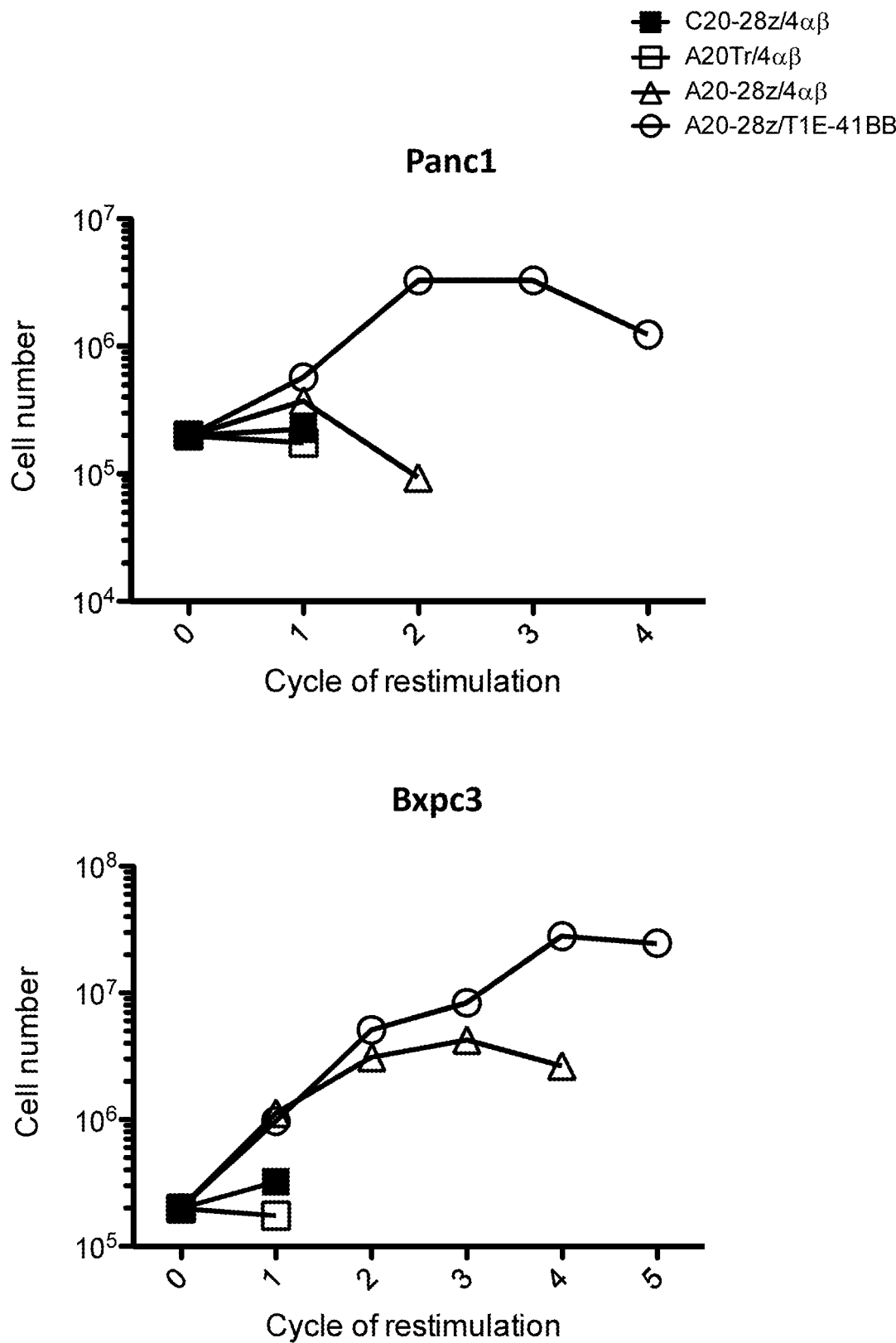
Figure 18B:
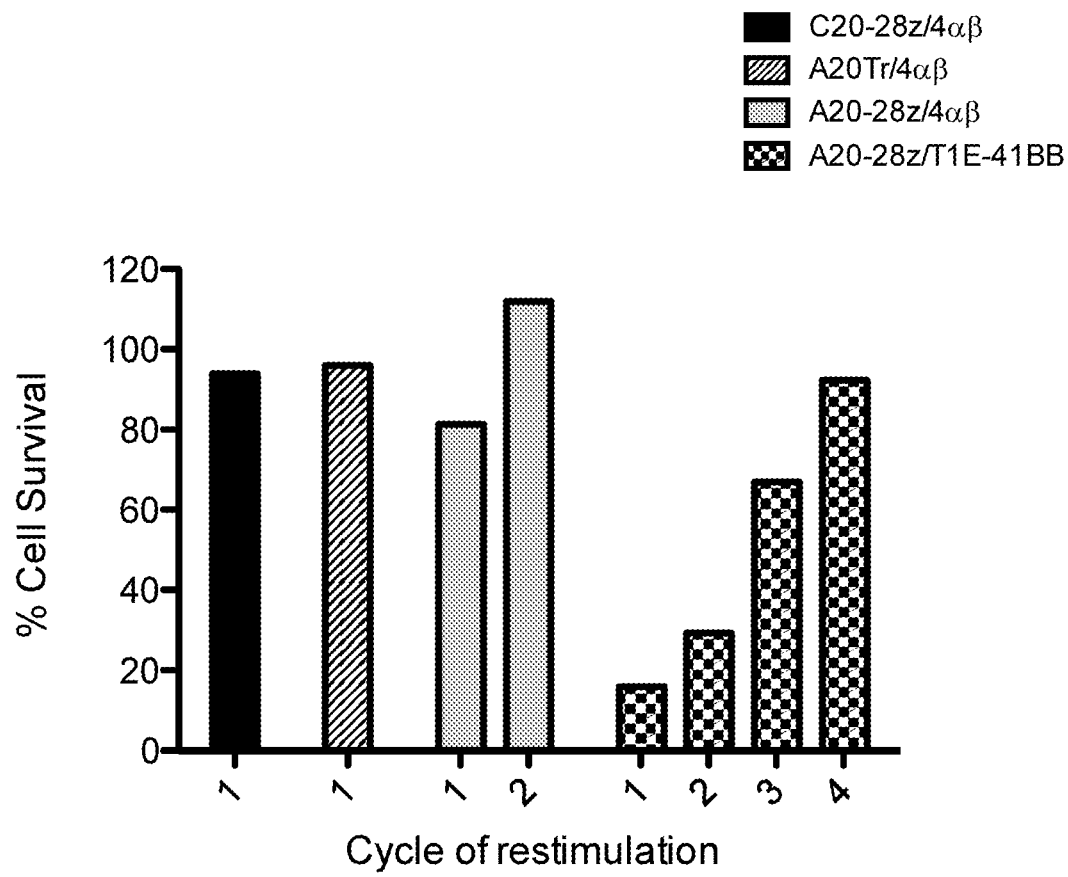
Figure 18B:
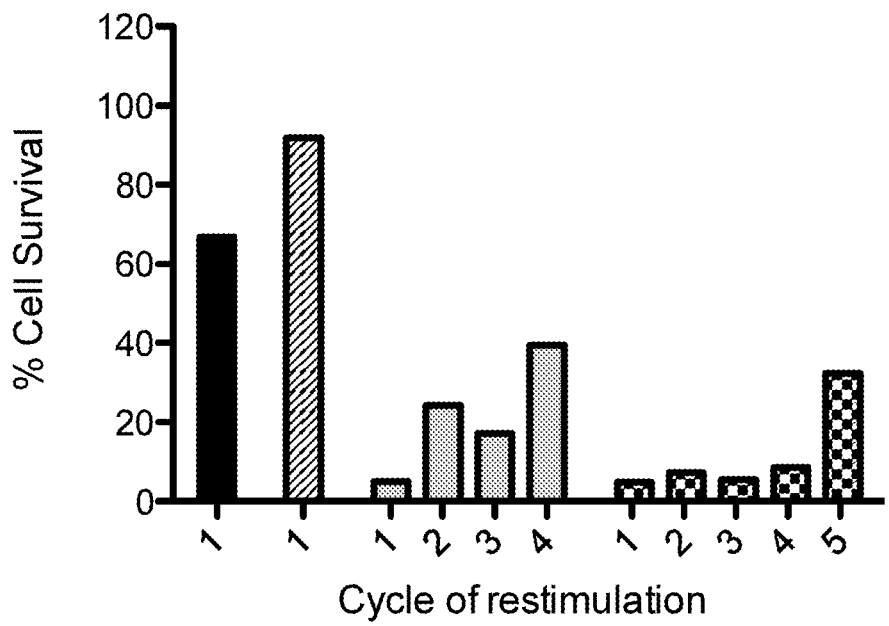

FIG. 18A,B shows the results of re-stimulation experiments using the CAR and pCAR-engineered T-cells described above and indicating the ability of A20-28z/T1E-41BB pCAR T-cells to undergo repeated antigen stimulation, accompanied by expansion of T-cells and destruction of target cells that do (Bxpc3) or do not (Panc1) express the αvβ6 integrin.

Figure 19A:
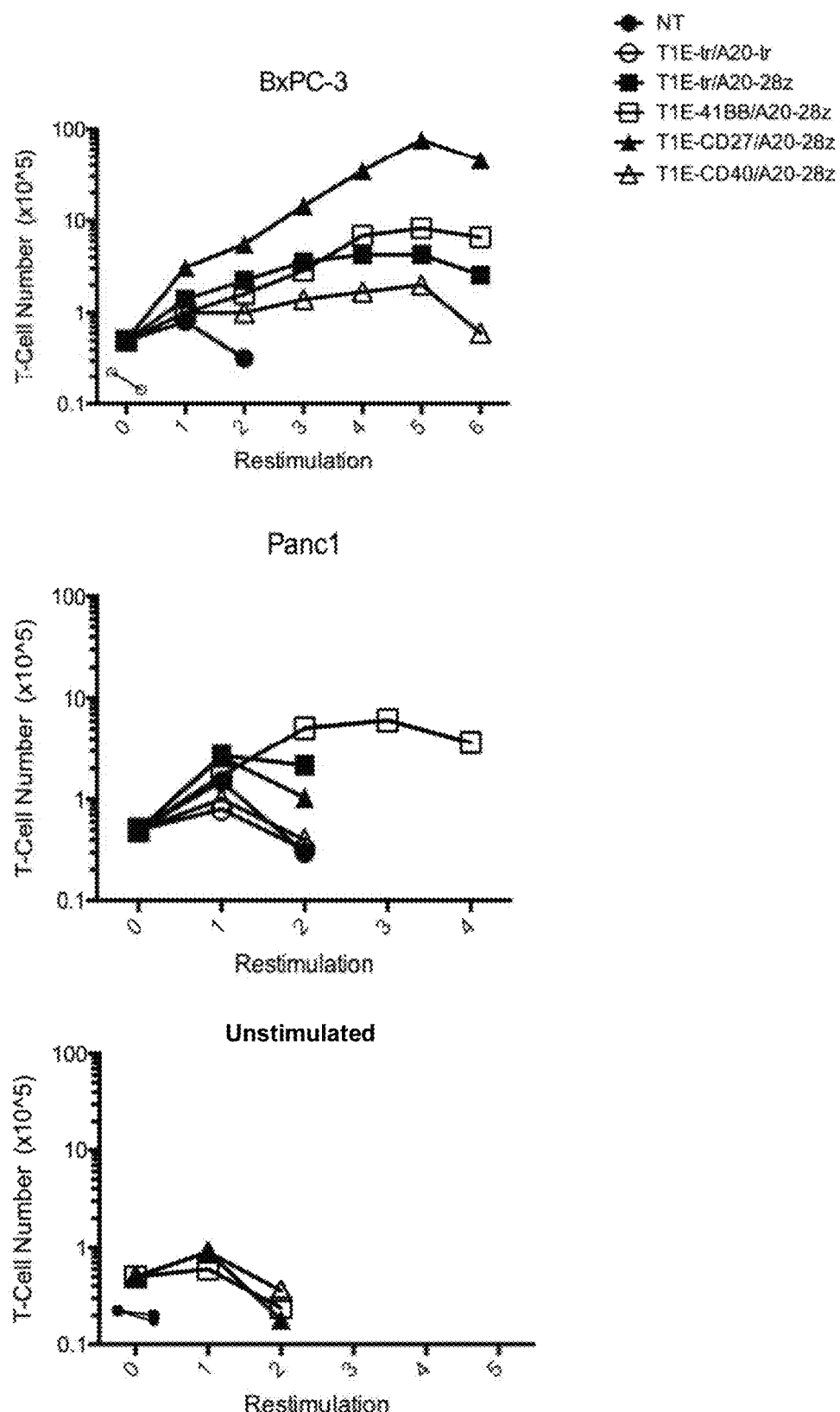

FIG. 19A,B shows the results of re-stimulation experiments using pCAR-engineered T-cells in which A20-28z was co-expressed with TIE-41BB, T1E-CD27 or T1E-CD40, allowing the comparative evaluation of co-stimulation by additional members of the TNF receptor family. Control T-cells were non-transduced (NT) while CARs contained truncated (tr) endodomains. T-cells were re-stimulated on target cells that do (Bxpc3) or do not (Panc1) express the αvβ6 integrin, making comparison with unstimulated T-cells. In the case of Bxpc3 cells, superior expansion (FIG. 19A) accompanied by sustained cytotoxic activity (FIG. 19B) was observed with A20-28z/T1E-CD27 T-cells. By contrast, with Panc1 cells, superior expansion (FIG. 19A) accompanied by sustained cytotoxic activity (FIG. 19B) was observed with A20-28z/T1E-CD27 T-cells. These data demonstrate that additional members of the TNF receptor family can also deliver co-stimulation using the pCAR format.

EXAMPLE 1

Figure 1A:
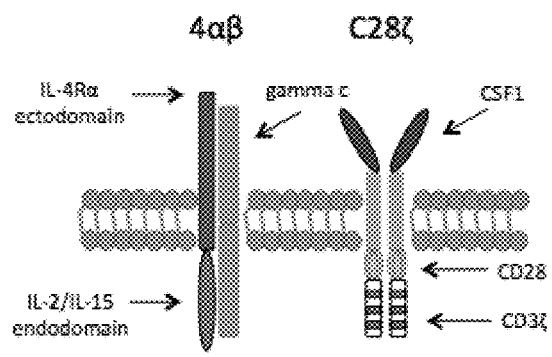
Figure 1A:
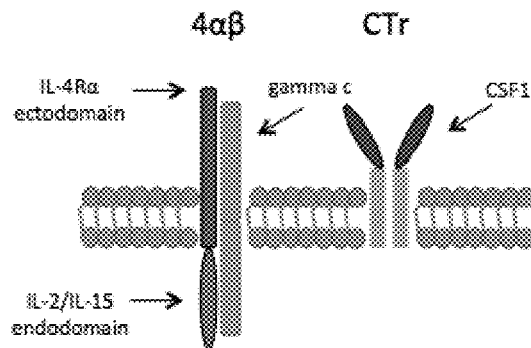
Figure 1A:
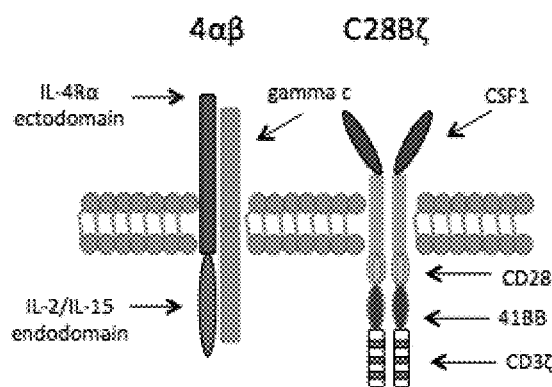
Figure 1A:
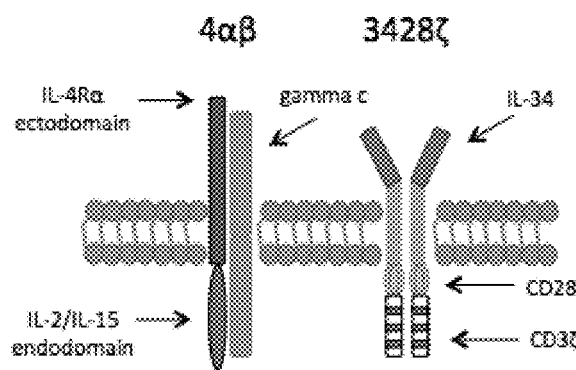
Figure 1A:
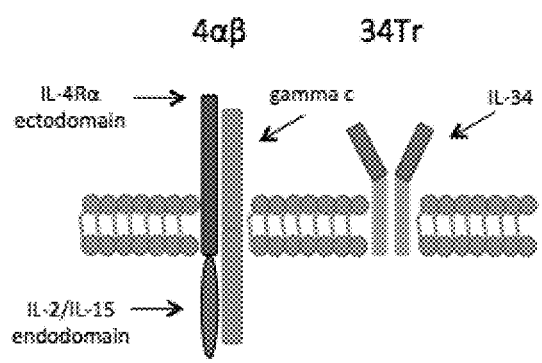
Figure 1A:
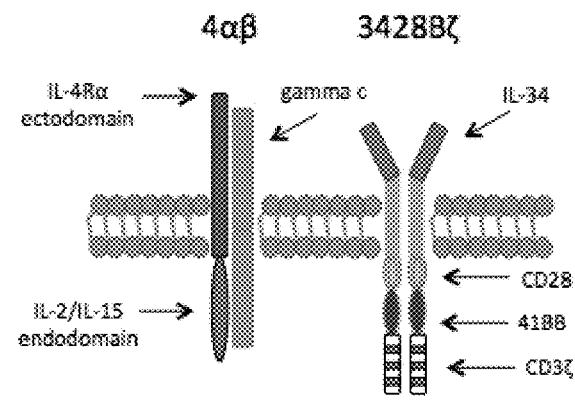
Figure 1B:
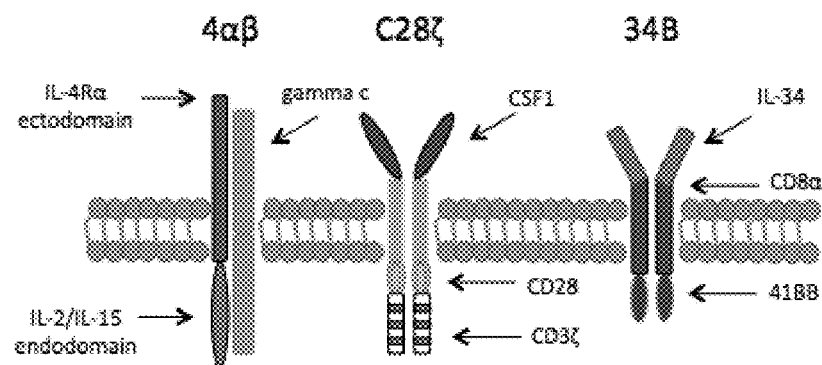
Figure 1B:
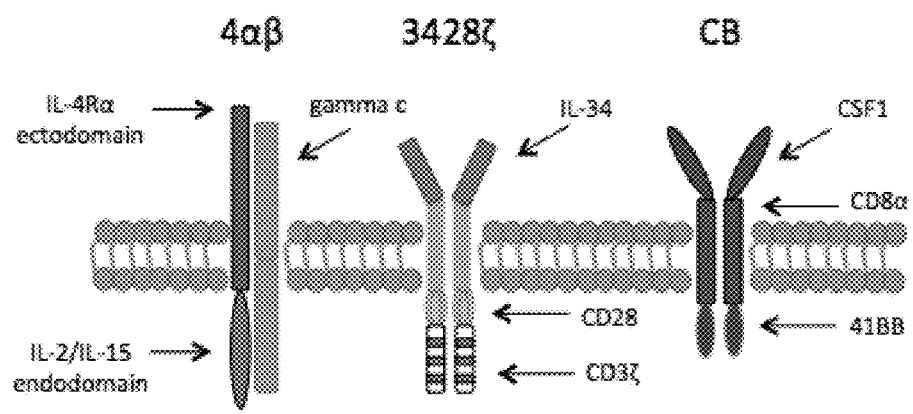

A panel of CARs targeted against the CSF-1 receptor (encoded by c-FMS), which is over-expressed in Hodgkin's lymphoma, anaplastic large cell lymphoma and some solid tumours such as triple negative breast cancer were prepared and are illustrated schematically in FIG. 1A,B. The panel of CARs included both second and third generation CARs with either of the two natural ligands, CSF-1 or IL-34, as the targeting moieties. Although both CSF-1 and IL-34 bind to CSF-1 receptor, IL-34 binds with much higher affinity (34-fold higher than CSF-1).

The constructs SFG C284 and SFG CTr were cloned in the SFG retroviral vector as NcoI/XhoI fragments, ensuring that their start codons are at the site of the naturally occurring NcoI site, previously occupied by the deleted env gene. Gene expression is achieved from the Moloney murine leukaemia virus (MoMLV) long terminal repeat (LTR), which has promoter activity and virus packaging of the RNA is ensured by the MoMLV tp packaging signal, which is flanked by splice donor and acceptor sites.

All other constructs were designed and cloned using the Polymerase Incomplete Primer Extension (PIPE) cloning method. PIPE cloning method is a PCR-based alternative to conventional restriction enzyme- and ligation-dependent cloning methods. It eliminates the need to incorporate restriction sites, which could encode additional unwanted residues into expressed proteins. The PIPE method relies on the inefficiency of the amplification process in the final cycles of a PCR reaction, possibly due to the decreasing availability of dNTPs, which results in the generation of partially single-stranded (PIPE) PCR products with overhanging 5'ends. A set of vector-specific primers was used for PCR vector linearization and another set of primers with 5'-vector-end overlapping sequences then used for insert amplification, generating incomplete extension products by PIPE. In a following step, the PIPE products were mixed and the single-stranded overlapping sequences annealed and assembled as a complete SFG CAR construct. Successful cloning was confirmed by diagnostic restriction digestion. DNA sequencing was performed on all constructs to confirm that the predicted coding sequence was present, without any PCR-induced mutations (Source Bioscience, UK).

The panel included two "dual targeted" Chimeric Activating Receptors (pCARS) In which CSF-1 or IL-34 are coupled to 28z and 4-1BB, or vice versa. The dual targeted pCAR combinations were then stochiometrically co-expressed in the same T-cell population using a Thosea Asigna (T)2A-containing retroviral vector. One of these CARs was designated 'C34B' (CSF1-28z plus IL34-41BB) and the other was named '34CB' (IL34-28z plus CSF1-41BB).

In these dual targeted CAR T-cells, both co-stimulatory motifs (CD28/4-1BB) are placed in their natural location, close to the membrane, physically separated from each other and co-expressed in the same T-cell.

All CARs were co-expressed with an IL-4 responsive 4αβ receptor using an additional T2A element in the vector. This enables enrichment/expansion of T-cells using IL-4, making it easier to compare the function of these diverse cell populations after selection.

The main focus of the experiments was to test the behaviour of the T-cells on repeated re-stimulation with tumour target cells that either express or lack the FMS/CSF-1 receptor target. In each cycle, 1 million of the indicated IL-4 expanded CAR T-cells were suspended in RPMI+ human AB serum and cultured with a confluent monolayer (24 well dish) of the antigen-expressing target (T47D FMS) or antigen null target (T47D).

Thereafter, if the CAR T-cells had persisted and destroyed the monolayer, 1 million T-cells were removed and re-stimulated in an identical manner each week. Total cell number was extrapolated at each time-point depending on the expansion of T-cells that occurred in each weekly cycle.

Throughout all of these experiments, T-cells were cultured in the absence of any exogenous cytokine such as IL-2 or IL-4—so they had to make their own cytokines in order to persist and expand. Cytokine (IFN-γ and IL-2) production was measured by ELISA in supernatants harvested from T-cell/tumour cell co-cultures, providing a second marker of effective co-stimulation.

Figure 2A:
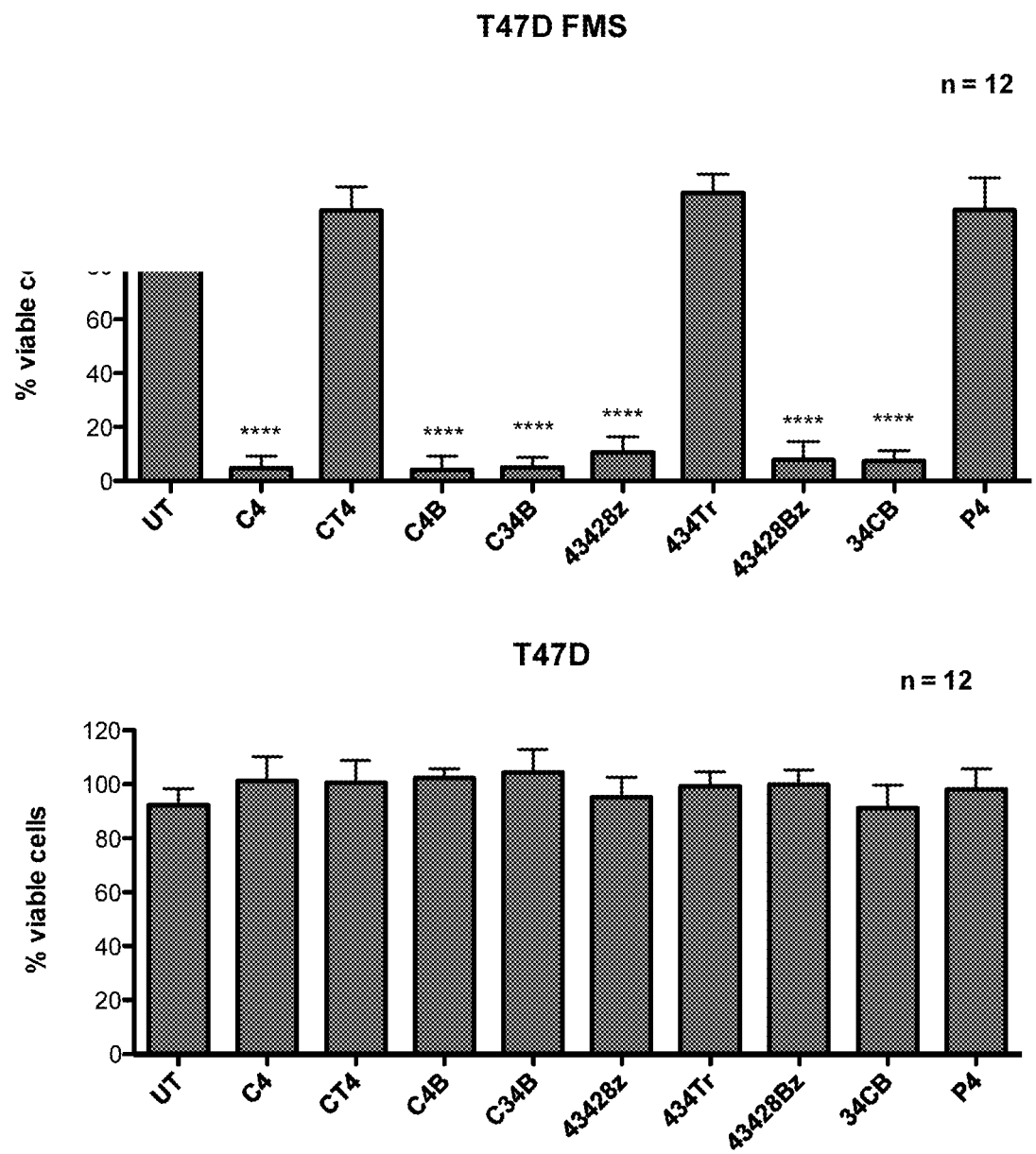
Figure 2B:
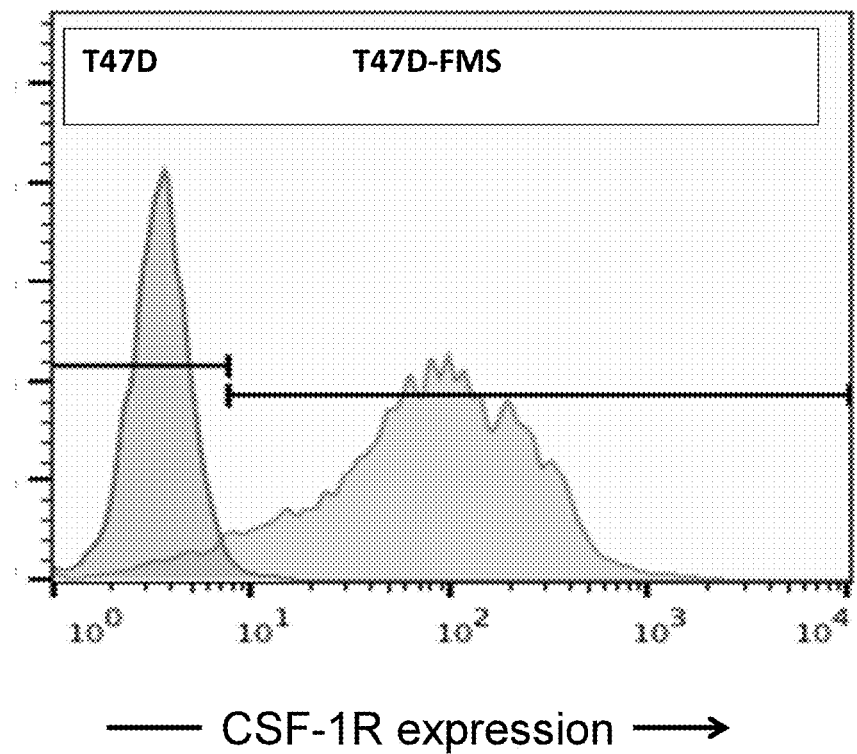

It was found (FIG. 2A,B) that on their first exposure to a tumour monolayer that expresses target (FMS encoded CSF-1 receptor), all CARs that are predicted to kill do so (pooled data from 12 expts). The controls are UT (untransduced), P4 (targets an irrelevant antigen, PSMA) and CT4 in which the endodomain is truncated. As expected, none of the CAR T-cells kill tumour cells that lack CSF-1 receptor (T47D).

Figure 3:
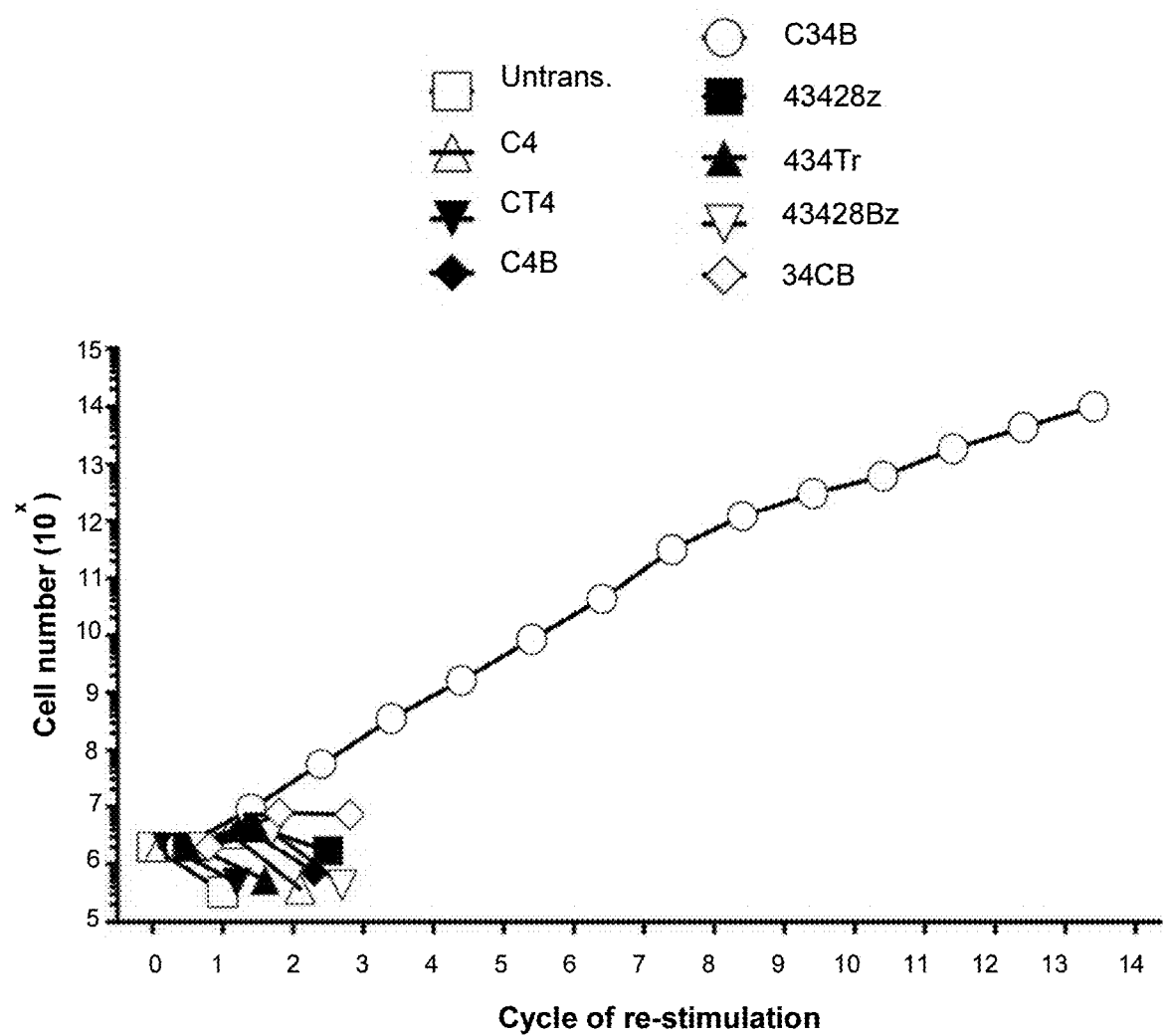
FIG. 3 shows a representative experiment in which T-cells that express CARs and pCARs of FIG. 1A,B (or untransduced) T-cells as control) were subjected to successive rounds of Ag stimulation in the absence of exogenous cytokine. Stimulation was provided by weekly culture on T47D FMS monolayers and T-cell numbers were enumerated at the indicated intervals.
Figure 4:
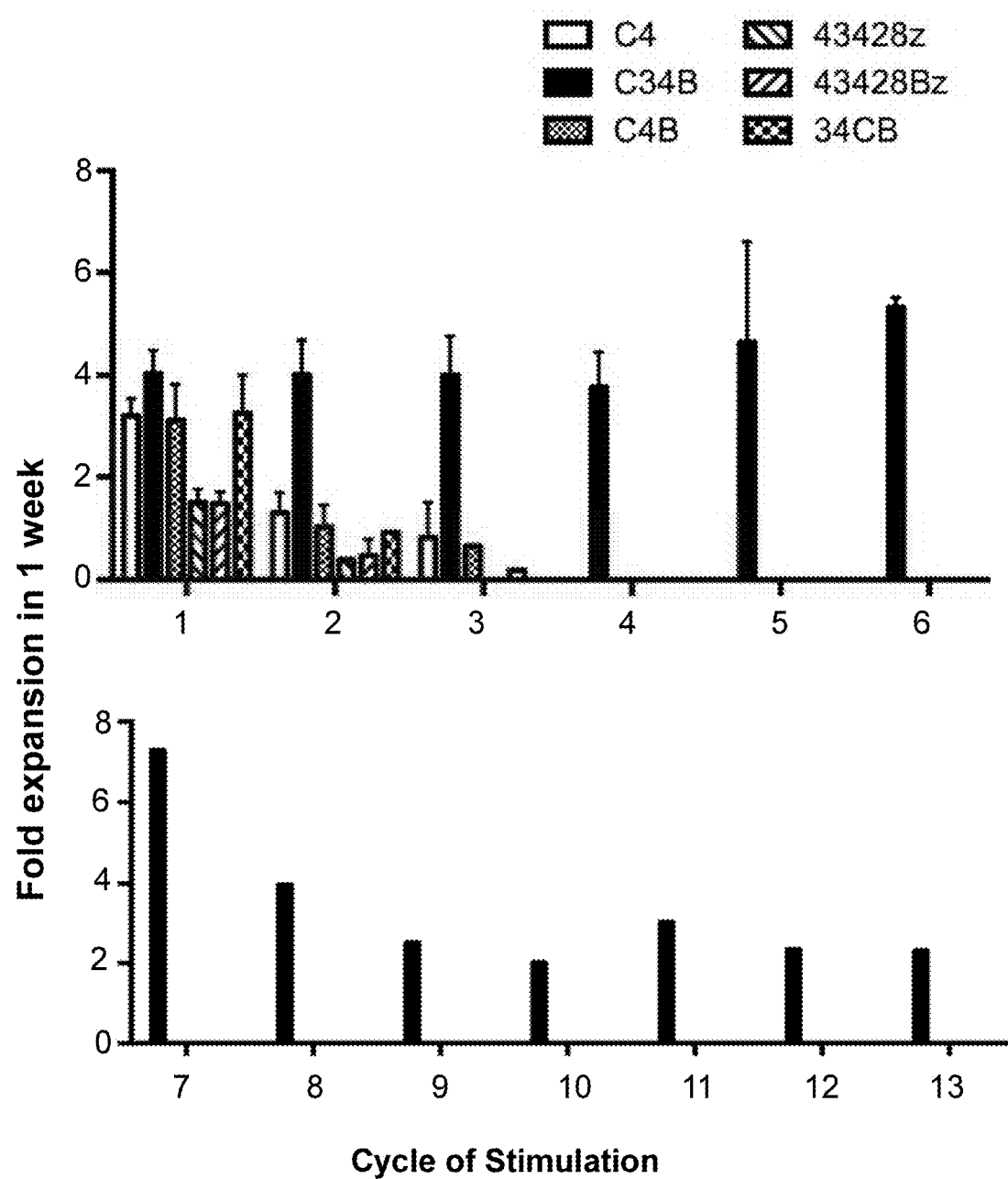
FIG. 4 shows pooled data from 7 similar replicate experiments to that shown in FIG. 3, indicating the fold expansion of CAR T-cells that occurred in the week after each cycle of stimulation.

A representative re-stimulation experiment is shown in FIG. 3. Pooled re-stimulation data from 7 experiments is shown in FIG. 4. In this case, proliferation on the first cycle was similar for most of the constructs, although the IL-34 targeted second and third generation constructs were poorer. This may be because the affinity of the IL-34 targeting moiety is too high.

In the later cycles however, the C34B dual pCAR combination (a CSF-1 targeted 28z second generation CAR co-expressed with an IL-34 targeted 4-1BB co-stimulatory motif) consistently emerged as clearly superior.

In the experiment shown in FIG. 3, supernatant was collected 24 hours after the time of each re-stimulation cycle and was analysed for cytokine content (IFN-γ and IL-2) by ELISA. The percentage of residual tumour cell viability was measured by MTT assay (representative examples shown in FIG. 5). The cytokine production results are shown in FIG. 6. It was found that only the C34B CAR T-cells retained the ability to make IL-2 throughout each cycle of stimulation. This was lost by all of the other CAR combinations after the first cycle. Sustained retention of the ability to make IL-2 through recursive re-stimulation is not usually seen with CAR T-cells and this suggests that this delivery of dual co-stimulation is fundamentally altering the differentiation of these cells in vitro, delaying the onset of anergy.

Figure 5:
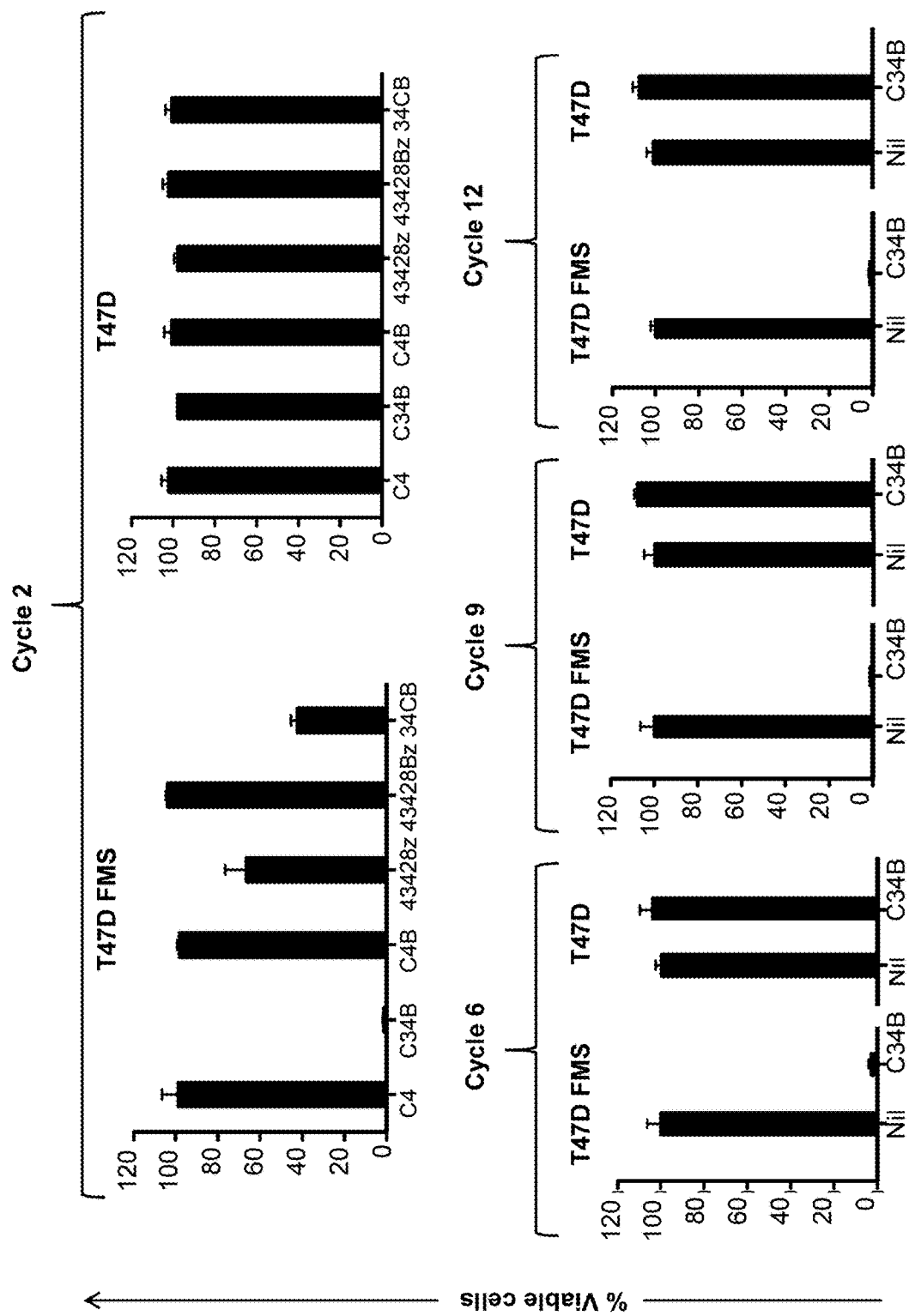
FIG. 5 shows illustrative cytotoxicity assays performed at the time of stimulation cycles 2, 6, 9 and 12 in the experiment shown in FIG. 3. This follows from the testing of T-cells for their ability to kill T47D FMS and unmodified T47D monolayers (MTT assay), twenty four hours after the time of each re-stimulation cycle.
Figure 6:
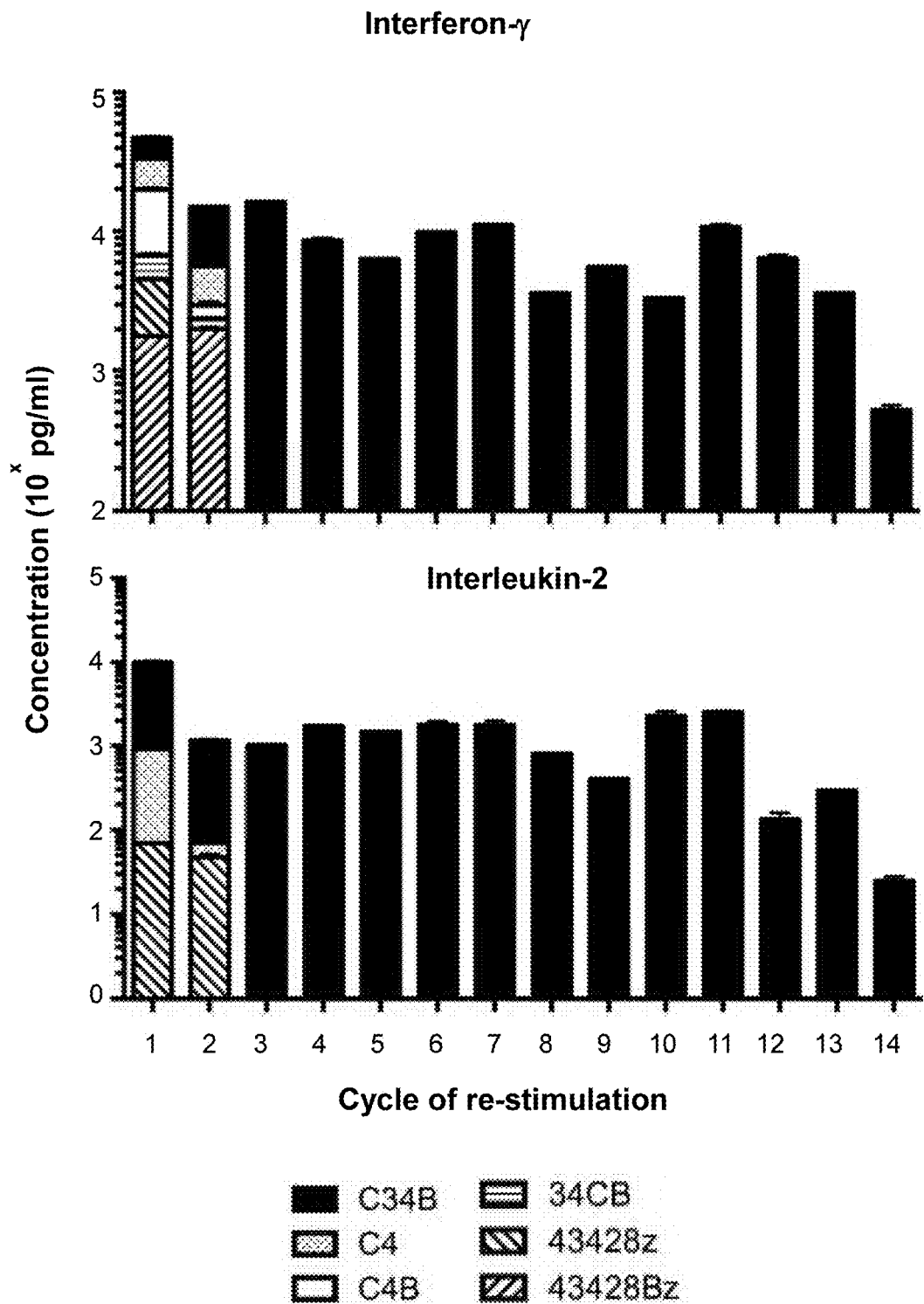
FIG. 6 shows the results of testing of supernatant, removed from cultures one day after each cycle of stimulation, for IL-2 and IFN-γ content by ELISA.

Number of viable T-cells post monolayer destruction on consecutive cycles of Ag-stimulation was also monitored and the results are shown in FIG. 5. After the second cycle of re-stimulation, all CARs except C34B begin to lose the ability to achieve CSF-1R-dependent tumour cell killing. By contrast, T-cells that express C34B retain antigen-dependent potency in this cytotoxic assay for up to 13 iterative cycles of re-stimulation, but never elicit cytotoxicity against unmodified T47D cells.

Also, so-called "exhaustion markers" on these T-cells (PD1, TIM3, 2B4 and LAG3) were also measured by flow cytometry. The results are shown in FIGS. 10-13. As expected, the percentage of T cells that expressed various exhaustion markers progressively increased on the re-stimulated T-cells, but this did not retard the proliferation, tumour cell destruction or cytokine release by the C34B cells, upon antigen stimulation. This suggests that the superior function of C34B is not the result of delayed upregulation of exhaustion markers.

In summary, the pCAR approach of the invention seems to maintain the cells in a state whereby they retain responsiveness to antigen through more cycles of re-stimulation. There are indications that it may retard differentiation beyond controlled memory state and it appears to delay the onset of anergy while retaining the ability of the cells to make IL-2 upon activation.

EXAMPLE 2

Analysis of Effects In Vivo

A panel of CARs used in Example 1 above were tested for anti-tumour activity using a highly aggressive in vivo xenograft model in which the CSF-1 receptor target is expressed at low levels and in which disease is disseminated throughout lymph nodes (FIG. 7A-D). Tumour cells were tagged with firefly luciferase, allowing the non-invasive monitoring of disease burden.

SCID/Beige mice were randomised into 6 groups (9 animals per group combined over two independent experiments) and were inoculated intravenously (IV) with $2\times10^6$ K299 tumour cells, re-suspended in 200 μL PBS. On day 5, the groups were treated with one of the therapeutic regimens indicated below:

C4B group: $20\times10^6$ C4B T-cells IV
C34B group: $20\times10^6$ C34B T-cells IV
43428Bz: $20\times10^6$ 43428Bz T-cells IV
34CB group: $20\times10^6$ 34CB T-cells IV
UT (Untransduced) group: $20\times10^6$ untransduced T-cells IV
NT (Non-treated) group: 200 μL PBS IV Tumour growth was monitored using bioluminescence imaging (BLI) at appropriate time-points for the duration of the study.

The results are shown in FIG. 8A,B. Again, the best performing system was that of the pCAR, C34B, indicated by lower average BLI emission (FIG. 8A-B), delayed tumour progression or tumour regression, leading to prolonged survival of mice (FIG. 8A).

Animals were weighed throughout the experiment and no significant toxicity was noted (FIG. 9).

EXAMPLE 3

Selection of Targeting Moieties to Engineer pCARs that Elicit T-Cell Activation in an αvβ6-Dependent Manner.

A panel of CARs that target αvβ6 integrin alone or together with the extended ErbB family were prepared and are shown schematically in FIG. 14. The binding element used in this case was A20 peptide (SEQ ID NO 11) derived from the GH-loop of the capsid protein VP1 from Foot and Mouth Disease Virus (serotype 01 BFS) (U.S. Pat. No. 8,927,501). This was placed downstream of a CD124 signal peptide and fused to CD28 and CD3 endodomains to form A20-28, a 2nd generation CAR. A control (C20-28ζ) was prepared comprising a similar construct but with a scrambled targeting peptide (named C20) in which the key RGDL motif was replaced with AAAA. A second control comprised A20 fused to a CD28 truncated endodomain (A20-Tr).

To create the pCAR of the invention (named TIE-41BB/A20-28z), A20-28z was co-expressed with a chimeric co-stimulatory receptor comprising a pan-ErbB targeted peptide (T1E) fused to a CD8α transmembrane and a 41BB endodomain.

Where indicated, CARs were co-expressed with the 4αβ chimeric cytokine receptor to allow for IL-4-mediated enrichment in vitro. Equimolar co-expression of the IL-4-responsive 4αβ chimeric cytokine receptor, in which the IL-4 receptor α ectodomain is fused to the transmembrane and endodomain of the shared IL-2/15 receptor β, was achieved using a Thosea Asigna (T)2A ribosomal skip peptide. These chimeric molecules were expressed in human T-cells by retroviral gene transfer.

The integrin expression pattern of cancer cell lines A375 was assessed using flow cytometry (FIG. 15A,B), and these were separated into αvβ6-negative (Panc1 and A375 puro) or αvβ6-positive (Bxpc3 and A375 puro 06) tumour cells.

These cells were co-cultured with CAR T-cells at an effector:target ratio of 1:1 for either 24, 28 or 72 hours, after which time, cytotoxicity was assessed by MTT assay and expressed relative to untreated tumour cells. The results are shown in FIG. 16A,B.

These data show that A20-28z CAR T-cells kill all target cells that express αvβ6 Integrin (Bxpc3 and A375β6 puro), but spare targets that lack this integrin (Panc1 and A375 puro). Secondly, the control CARs C20-28z and A20-Tr are inactive in these assays. Thirdly, T-cells that express the T1E-41BB/A20-28z pCAR cause efficient killing of target cells that express αvβ6 integrin (Bxpc3 and A375 β6 puro). All of these results are as expected. Notably however, T-cells that express the T1E-41BB/A20-28z pCAR also cause the killing of target cells that lack αvβ6 (Panc1 and A375 puro). This indicates that, within a pCAR configuration, the ability of the A20 peptide to bind non-αvβ6 integrins with low affinity is sufficient to trigger the activation of these engineered T-cells.

Production of IFN-γ by the pCAR and control engineered T-cells was then assessed. Tumour cells that lacked αvβ6 (Panc1 and A375 puro) or expressed αvβ6 (Bxpc3 and A375 puro 06) were co-cultured with genetically engineered T-cells at an effector:target ratio of 1:1 and supernatant was collected after 24, 48 or 72 hours. Levels of IFN-γ were quantified by ELISA (eBioscience). The results are shown in FIG. 17A,B. As expected, the controls did not generate significant quantities of IFN-γ while A20-28z CAR T-cells released IFN-γ when cultured with αvβ6-positive (Bxpc3 and A375 puro β6) tumour cells. Notably, T-cells that express the pCAR of the invention, T1E-41BB/A20z, produce more IFN-γ than A20-28z T-cells when cultured with αvβ6-positive (Bxpc3) tumour cells. In addition, T1E-41BB/A20z$^+$ T-cells produced IFN-γ when cultured with αvβ6-negative (Panc1 and A375 puro) tumour cells. Once again, this demonstrates that, within a pCAR configuration, low affinity binding of the A20 peptide to non-αvβ6 integrins is sufficient to trigger the activation of these engineered T-cells.

Next, the CAR T-cell populations were re-stimulated bi-weekly in the absence of IL-2 support on Panc1 (αvβ6 negative) or Bxpc3 tumour cells (αvβ6 positive). Tumour cells were co-cultured with CAR T-cells derived from a patient with pancreatic ductal adenocarcinoma (PDAC) at an effector:target ratio of 1:1 (FIG. 18A,B). T-cells were initially added at 2×10$^5$ cells/well and were counted 72 hrs after co-culture to assess expansion (top panels). Cytotoxicity was assessed at 72 hrs post-addition of T-cells by MTT assay (bottom panels). If there were a sufficient number of T-cells (2×10$^5$), T-cells were re-stimulated on a fresh tumour monolayer and the process repeated a further 72 hrs later.

Results are shown in FIG. 18A,B. These illustrate that A20-28z/T1E-41BB$^+$ T-cells undergo a number of rounds of expansion accompanied by IL-2 release (data not shown) and destruction of αvβ6$^+$ Bxpc3 cells. Once again, they also underwent a number of rounds of expansion accompanied by IL-2 release and destruction of Panc1 tumour cells.

Overall, the results clearly showed that the pCAR comprising A20-28z/T1E-41BB exhibits enhanced in vitro functionality compared to a 2$^{nd}$ generation CAR targeted against αvβ6. Furthermore, the A20-28z/T1E-41BB$^+$ T-cells also undergo activation by Panc1 or A375 puro cells, which express minimal to undetectable levels of this integrin. Taken with the findings obtained using the C34B pCAR (examples 1 and 2), this indicates that the pCAR configuration allows T-cell activation to occur upon serial re-stimulation when a high affinity binding interaction occurs with the 41BB CCR while a lower affinity interaction occurs with the 28z 2$^{nd}$ generation CAR.

EXAMPLE 4

Use of an Alternative TNF Receptor Family Member, CD27 to Engineer a Functional pCAR.

Figure 19B:
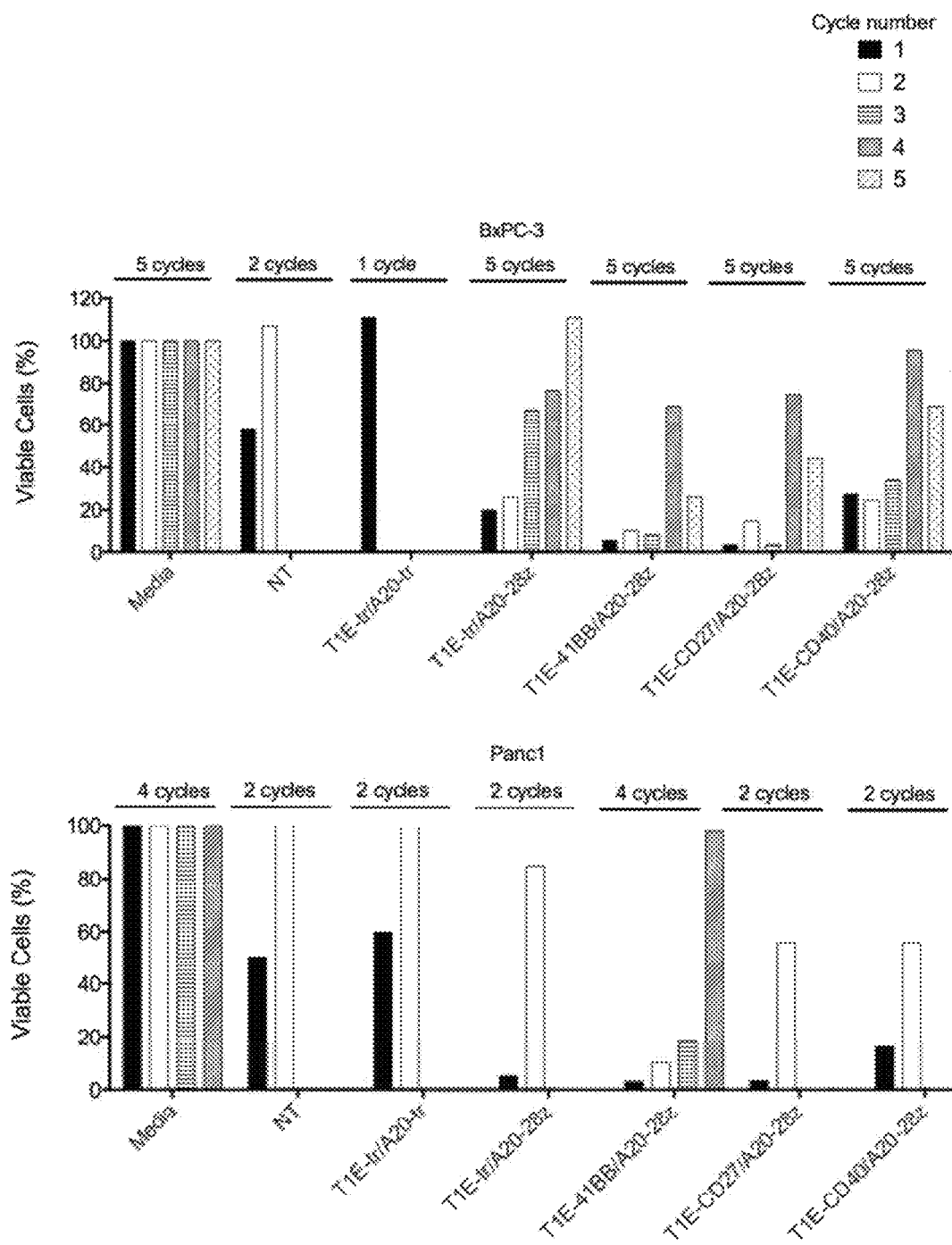

Using the A20-28z/T1E-41BB pCAR as starting material, additional pCARs were engineered in which the 41BB module was replaced by alternative members of the TNF receptor family, namely CD27 or CD40. Control pCARs were engineered in which endodomains were truncated (tr). Target cells that express (Bxpc3) or lack (Panc1) αvβ6 were plated at a density of 5×10$^4$ cells per well of a 24 well plate. After 24 hours, 5×10 pCAR T-cells were added to target cells or empty wells ("unstimulated"), without exogenous cytokine support. After a further 72 hours, T-cells were harvested from the wells and were counted (FIG. 19A). An MTT assay was performed to determine the percentage viability of the residual target cells, making comparison with control target cells that had been plated without addition of T-cells (FIG. 19B). If T-cells proliferated after each cycle of stimulation, they were re-stimulated on fresh target cells, exactly as described above. Proliferation of pCAR T-cells (FIG. 19A) and MTT assay (FIG. 19B) were performed after 72 hours as before. Iterative re-stimulation of pCAR T-cells and assessment of target cell killing was continued in this manner until T-cells no longer proliferated over the course of each 72 hour cycle.

These data once again confirm the superior functionality of the A20-28z/T1E-41BB pCAR when T-cells are stimulated on Panc1 target cells, indicated by sustained T-cell proliferation and tumour cell killing. This provides further confirmation that low affinity binding of the A20 peptide to non-αvβ6 integrins is sufficient to trigger the activation of these engineered T-cells. Notably however, the A20-28z/T1E-CD27 pCAR achieved the greatest level of proliferation (FIG. 19A) and sustained tumour cell killing (FIG. 19B) when re-stimulated on αvβ6-expressing Bxpc3 cells. By contrast, CD40-based pCARs exhibited modest function in these assays. Together, these data demonstrate that a number of TNF receptor family members can be employed to engineer pCARs that demonstrate superior functionality, exemplified by CD27 or 41BB.

The invention claimed is:

1. An isolated immuno-responsive cell expressing:
   (i) a second generation chimeric antigen receptor comprising:
      (a) a signalling region, wherein the signalling region comprises the intracellular domain of human CD3ζ chain or a variant thereof;
      (b) a co-stimulatory signalling region, wherein the co-stimulatory signalling region is the co-stimulatory region of CD28;
      (c) a transmembrane domain, wherein the transmembrane domain is a CD28 transmembrane domain; and
      (d) a binding element that specifically interacts with a first epitope on a target antigen, wherein the binding element is T1E or a scFv; and
   (ii) a chimeric costimulatory receptor comprising:
      (e) a co-stimulatory signalling region, wherein the costimulatory signalling region is the costimulatory signalling region of 4-1BB;
      (f) a transmembrane domain, wherein the transmembrane domain is a CD8α transmembrane domain; and
      (g) a binding element that specifically interacts with a second epitope on a target antigen, wherein the binding element is T1E or a scFv.

2. The isolated immuno-responsive cell of claim 1, wherein the binding element (d) is a scFv.

3. The isolated immuno-responsive cell of claim 1, wherein the binding element (d) is T1E.

4. The isolated immuno-responsive cell of claim 1, wherein the binding element (g) is a scFv.

5. The isolated immuno-responsive cell of claim 1, wherein the binding element (g) is T1E.

6. The isolated immuno-responsive cell of claim 2, wherein the binding element (g) is a scFv.

7. The isolated immuno-responsive cell of claim 2, wherein the binding element (g) is T1E.

8. The isolated immuno-responsive cell of claim 3, wherein the binding element (g) is a scFv.

9. The isolated immuno-responsive cell of claim 3, wherein the binding element (g) is T1E.

10. The isolated immuno-responsive cell of claim 1, wherein the cell is a T-cell.

11. The isolated immuno-responsive cell of claim 10, wherein the T-cell is a CD8+ T-cell.

12. The isolated immuno-responsive cell of claim 10, wherein the T-cell is a CD4+ T-cell.

13. The isolated immuno-responsive cell of claim 1, wherein the cell is an NK cell.

14. The isolated immuno-responsive cell of claim 2, wherein the cell is a T-cell.

15. The isolated immuno-responsive cell of claim 14, wherein the T-cell is a CD8+ T-cell.

16. The isolated immuno-responsive cell of claim 14, wherein the T-cell is a CD4+ T-cell.

17. The isolated immuno-responsive cell of claim 2, wherein the cell is an NK cell.

18. The isolated immuno-responsive cell of claim 3, wherein the cell is a T-cell.

19. The isolated immuno-responsive cell of claim 18, wherein the T-cell is a CD8+ T-cell.

20. The isolated immuno-responsive cell of claim 18, wherein the T-cell is a CD4+ T-cell.

21. The isolated immuno-responsive cell of claim 3, wherein the cell is an NK cell.

22. The isolated immuno-responsive cell of claim 1, wherein the cell co-expresses a chimeric cytokine receptor.

23. The isolated immuno-responsive cell of claim 22, wherein the chimeric cytokine receptor is 4αβ.

24. The isolated immuno-responsive cell of claim 2, wherein the cell co-expresses a chimeric cytokine receptor.

25. The isolated immuno-responsive cell of claim 24, wherein the chimeric cytokine receptor is 4αβ.

26. The isolated immuno-responsive cell of claim 3, wherein the cell co-expresses a chimeric cytokine receptor.

27. The isolated immuno-responsive cell of claim 26, wherein the chimeric cytokine receptor is 4αβ.

28. A method for preparing the isolated immuno-responsive cell of claim 1, comprising transducing an immuno-responsive cell with nucleic acids encoding:
   (i) a second generation chimeric antigen receptor comprising:
      (a) a signalling region, wherein the signalling region comprises the intracellular domain of human CD3ζ chain or a variant thereof;
      (b) a co-stimulatory signalling region; wherein the co-stimulatory signalling region is the co-stimulatory region of CD28;
      (c) a transmembrane domain, wherein the transmembrane domain is a CD28 transmembrane domain; and
      (d) a binding element that specifically interacts with a first epitope on a target antigen, wherein the binding element is T1E or a scFv; and
   (ii) a chimeric costimulatory receptor comprising:
      (e) a co-stimulatory signalling region which is the costimulatory signalling region of 4-1BB;
      (f) a transmembrane domain, wherein the transmembrane domain is a CD8α transmembrane domain; and
      (g) a binding element that specifically interacts with a second epitope on a target antigen, wherein the binding element is T1E or a scFv.

29. The method of claim 28, wherein the immuno-responsive cell comprises a chimeric cytokine receptor, and wherein an expansion step is carried out in the presence of a cytokine.

* * * * *

SEQUENCE LISTING

<160> NUMBER OF SEQ ID NOS: 11

<210> SEQ ID NO 1
<211> LENGTH: 112
<212> TYPE: PRT
<213> ORGANISM: Homo sapiens

<400> SEQUENCE: 1

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys

```
                35                  40                  45
Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 2
<211> LENGTH: 112
<212> TYPE: PRT
<213> ORGANISM: Homo sapiens

<400> SEQUENCE: 2

Arg Val Lys Phe Ser Arg Ser Ala Glu Pro Pro Ala Tyr Gln Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 3
<211> LENGTH: 220
<212> TYPE: PRT
<213> ORGANISM: Homo sapiens

<400> SEQUENCE: 3

Met Leu Arg Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
                35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Pro Tyr Leu Asp Asn Glu Lys Ser
                115                 120                 125

Asn Gly Thr Ile Ile His Val Lys Gly Lys His Leu Cys Pro Ser Pro
                130                 135                 140

Leu Phe Pro Gly Pro Ser Lys Pro Phe Trp Val Leu Val Val Val Gly
```

```
                 145                 150                 155                 160
Gly Val Leu Ala Cys Tyr Ser Leu Leu Val Thr Val Ala Phe Ile Ile
                 165                 170                 175
Phe Trp Val Arg Ser Lys Arg Ser Arg Leu Leu His Ser Asp Tyr Met
                 180                 185                 190
Asn Met Thr Pro Arg Arg Pro Gly Pro Thr Arg Lys His Tyr Gln Pro
                 195                 200                 205
Tyr Ala Pro Pro Arg Asp Phe Ala Ala Tyr Arg Ser
    210                 215                 220

<210> SEQ ID NO 4
<211> LENGTH: 107
<212> TYPE: PRT
<213> ORGANISM: Homo sapiens

<400> SEQUENCE: 4

Ile Glu Val Met Tyr Pro Pro Pro Tyr Leu Asp Asn Glu Lys Ser Asn
1               5                   10                  15
Gly Thr Ile Ile His Val Lys Gly Lys His Leu Cys Pro Ser Pro Leu
            20                  25                  30
Phe Pro Gly Pro Ser Lys Pro Phe Trp Val Leu Val Val Val Gly Gly
        35                  40                  45
Val Leu Ala Cys Tyr Ser Leu Leu Val Thr Val Ala Phe Ile Ile Phe
    50                  55                  60
Trp Val Arg Ser Lys Arg Ser Arg Leu Leu His Ser Asp Tyr Met Asn
65                  70                  75                  80
Met Thr Pro Arg Arg Pro Gly Pro Thr Arg Lys His Tyr Gln Pro Tyr
                85                  90                  95
Ala Pro Pro Arg Asp Phe Ala Ala Tyr Arg Ser
            100                 105

<210> SEQ ID NO 5
<211> LENGTH: 10
<212> TYPE: PRT
<213> ORGANISM: Artificial Sequence
<220> FEATURE:
<223> OTHER INFORMATION: tag

<400> SEQUENCE: 5

Glu Gln Lys Leu Ile Ser Glu Glu Asp Leu
1               5                   10

<210> SEQ ID NO 6
<211> LENGTH: 111
<212> TYPE: PRT
<213> ORGANISM: Artificial Sequence
<220> FEATURE:
<223> OTHER INFORMATION: costimulatory signalling region

<400> SEQUENCE: 6

Ile Glu Val Glu Gln Lys Leu Ile Ser Glu Glu Asp Leu Leu Asp Asn
1               5                   10                  15
Glu Lys Ser Asn Gly Thr Ile Ile His Val Lys Gly Lys His Leu Cys
            20                  25                  30
Pro Ser Pro Leu Phe Pro Gly Pro Ser Lys Pro Phe Trp Val Leu Val
        35                  40                  45
Val Val Gly Gly Val Leu Ala Cys Tyr Ser Leu Leu Val Thr Val Ala
    50                  55                  60
Phe Ile Ile Phe Trp Val Arg Ser Lys Arg Ser Arg Leu Leu His Ser
```

```
            65                  70                  75                  80
Asp Tyr Met Asn Met Thr Pro Arg Arg Pro Gly Pro Thr Arg Lys His
                    85                  90                  95

Tyr Gln Pro Tyr Ala Pro Pro Arg Asp Phe Ala Ala Tyr Arg Ser
            100                 105                 110
```

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: SITE
<222> LOCATION: 5,6
<223> OTHER INFORMATION: Xaa is any amino acid residue

<400> SEQUENCE: 7

```
Arg Gly Asp Leu Xaa Xaa Leu
1               5
```

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: SITE
<222> LOCATION: 5,6
<223> OTHER INFORMATION: Xaa is any residue

<400> SEQUENCE: 8

```
Arg Gly Asp Leu Xaa Xaa Ile
1               5
```

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

```
Tyr Thr Ala Ser Ala Arg Gly Asp Leu Ala His Leu Thr Thr His
1               5                   10                  15

Ala Arg His Leu
            20
```

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide

<400> SEQUENCE: 10

```
Gly Phe Thr Thr Gly Arg Arg Gly Asp Leu Ala Thr Ile His Gly Met
1               5                   10                  15

Asn Arg Pro Phe
            20
```

<210> SEQ ID NO 11
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 11

Asn Ala Val Pro Asn Leu Arg Gly Asp Leu Gln Val Leu Ala Gln Lys
1               5                   10                  15

Val Ala Arg Thr
            20
```